US 7,119,079 B2
Oct. 10, 2006

United States Patent
Barbeau

(54) BIOADHESIVE PHARMACEUTICAL COMPOSITIONS

(76) Inventor: Donald L. Barbeau, 790 Frontage Rd., Northfield, IL (US) 60093

( * ) Notice: Subject to any disclaimer, the term of this patent is extended or adjusted under 35 U.S.C. 154(b) by 0 days.

This patent is subject to a terminal disclaimer.

(21) Appl. No.: 10/760,970

(22) Filed: Jan. 20, 2004

(65) Prior Publication Data

US 2004/0142880 A1 Jul. 22, 2004

Related U.S. Application Data

(63) Continuation-in-part of application No. 10/348,851, filed on Jan. 22, 2003, now Pat. No. 6,699,848.

(51) Int. Cl.
*A61K 31/715* (2006.01)
*A61K 31/70* (2006.01)
*C07H 5/04* (2006.01)

(52) U.S. Cl. .............................. 514/54; 514/25; 514/61; 514/62; 536/123.1; 536/4.1; 536/17.2; 536/18.7

(58) Field of Classification Search ................. 514/54, 514/25, 61, 62, 42; 536/123.1, 4.1, 17.2, 536/18.7, 22.1
See application file for complete search history.

(56) References Cited

U.S. PATENT DOCUMENTS

| 4,241,005 A | 12/1980 | Hussain et al. | |
|---|---|---|---|
| 4,496,533 A | 1/1985 | Halskov | |
| 4,880,794 A | 11/1989 | Halskov | |
| 6,699,848 B1 * | 3/2004 | Barbeau | 514/54 |

* cited by examiner

*Primary Examiner*—Shaojia Anna Jiang
*Assistant Examiner*—Michael C. Henry

(74) *Attorney, Agent, or Firm*—Schiff Hardin LLP

(57) ABSTRACT

Disclosed are compounds having the formula

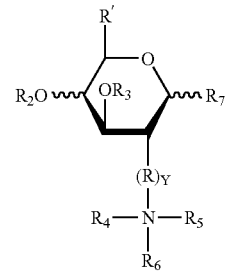

wherein $R_2$ is hydrogen, a monomeric glycoside or an oligomeric glycoside, $R_3$ is hydrogen, a monomeric glycoside, an oligomeric glycoside, or a group having the formula

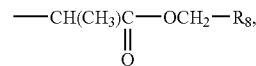

R is a lower alkylene, R' is selected from the group consisting of moieties having the formula

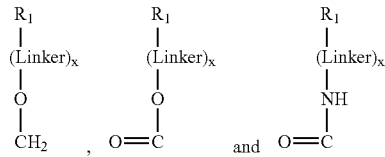

where X=0 or 1, Y=0 or 1, $R_1$ is hydrogen or a pharmacologically active drug residue, $R_8$ a pharmacologically active drug residue, $R_4$, $R_5$, and $R_6$ are independently hydrogen, alkyl, aryl, aralkyl, and cycloalkyl or together form a nitrogen-containing ring, and $R_7$ is hydroxyl or hydroxyalkyl.

19 Claims, 2 Drawing Sheets

BIOADHESIVE PHARMACEUTICAL COMPOSITIONS

CROSS-REFERENCE TO RELATED APPLICATIONS

This application is a continuation-in-part application to patent application Ser. No. 10/348,851 entitled Bioadhesive Anti-inflammatory Pharmaceutical Compositions, filed Jan. 22, 2003 now U.S. Pat. No. 6,669,848, in the name of Donald L. Barbeau.

BACKGROUND OF THE INVENTION

The present invention relates to novel pharmaceutical compounds having unique site-specific and site-retention properties. These pharmaceutical compounds are useful in the treatment of a number of medical disorders including infection, pain, menstrual abnormalities, glaucoma and inflammation. In one aspect, the present invention relates to novel anti-inflammatory compounds useful in the treatment of gastrointestinal inflammation. The invention further relates to a method of controlling the delivery of anti-inflammatory compounds, particularly mesalamine (5-amino salicylic acid, 5-ASA), 4-amino salicylic acid (4-ASA), and 3-amino salicylic acid (3-ASA) to the entire gastrointestinal (GI) tract in patients suffering from inflammatory bowel disease. The present invention principally relates to the treatment of inflammatory bowel diseases and functional bowel disorders with anti-inflammatory drugs such as mesalamine (5-ASA). Unlike conventional and well established treatments, which rely on timed-release, bacteria-mediated hydrolysis and/or pH dependent release formulations that have restricted access to gastrointestinally inflamed tissue, the compositions of the present invention can target a site throughout the length of the gastrointestinal intestinal tract to consistently deliver the medicine where it will be clinically most effective.

The ability of mesalamine to reduce inflammation is well established; however, its clinical efficacy for the treatment of certain inflammatory bowel diseases is not compelling because its pharmacological activity is dependent on where the drug is released in the intestinal tract. It is believed that mesalamine inhibits the production of leukotrienes and prostaglandins from arachidonic acid through a local effect at the sites of bowel inflammation; however, pre-clinical and clinical studies with current mesalamine products suggest these formulations have a variable release throughout the intestinal tract and are not retained at the inflammatory sites for a time sufficient to reduce inflammation. Moreover, the differences in the site of drug release (duodenum, jejunum, ileum or colon) from these formulations results in dramatically different absorption and metabolism of the drug. The variations in drug release and drug retention at different locations within the bowel from these commercial formulations makes it particularly difficult to treat patients having locally induced inflammation that differs from the release location.

Treating patients with anti-inflammatory compounds with gastrointestinal inflammation is not new, and the Food and Drug Administration (FDA) has already approved treating patients with mesalamine for certain types of inflammatory bowel disease that occur in the colon, namely ulcerative colitis. A number of different oral or rectal mesalamine formulations are commercially available for the treatment of inflammation in ulcerative colitis; however, each has met with limited success in ameliorating the symptoms of Crohn's disease. The principal difficulties with currently available mesalamine formulations include the inability to consistently release mesalamine at the inflamed tissue in different patients and the inability to locally deliver mesalamine to the site of inflammation for a time effective in reducing inflammation. The latter is due, in part, to extensive absorption and deactivation of mesalamine in the proximal ileum. Ironically, the clinical success of mesalamine formulations in treating inflammation in the colon has fostered the development of additional mesalamine formulations that only release the drug in the colon.

In the treatment of distal colitis, an enema preparation of mesalamine (Rowasa® enema) is considered efficacious. In the initial study to identify the active moiety in sulfasalazine, patients with distal ulcerative colitis were treated with sulfasalazine, mesalamine, or sulfapyridine enemas. Three quarters of the patients in the sulfasalazine and mesalamine groups showed improvement, while only about one third of patients in the sulfapyridine group improved. These data supported the hypothesis that mesalamine was the active therapeutic moiety, and subsequent studies confirmed the efficacy of mesalamine enemas in distal colitis. (Azad Khan et al. Lancet 2:892–895 (1977); Physician's Desk Reference 55$^{th}$ Edition pp 3160–3162, publ. Medical Economics (2001); U.S. Pat. No. 4,496,553).

Mesalamine, rectally administered through an enema, has limited systemic absorption and consequently good topical effectiveness in treating inflammation in the colon; however, rectally administered mesalamine acts only locally on the recto-sigmoidal colon so that more proximal inflammation cannot be treated in this manner. Moreover, patient compliance with rectally administered mesalamine is low, and has been associated with an increase colon cancer. Oral delivery of mesalamine is the preferred route of administration; however, suitable formulations have been elusive. Oral delivery of mesalamine to sites of inflammation located above the transverse colon, and particularly to the proximal small bowel, is more complex and successful delivery and therapeutic benefit depends upon factors such as gastric emptying time and retention time in the intestinal lumen. Gastric emptying time varies from one individual to another and in the same individual may vary according to the size of (orally taken) particles (or tablets) and according to whether the patient is in a fasting or non-fasting state. Dwell time in the ileum is also variable and particularly important in previously surgically treated Crohn's patients having a shortened small bowel. Luminal retention is related to the absorption and metabolism of mesalamine in the upper portion of the small intestine.

Another difficulty in formulating oral mesalamine for accurate targeting is stomach acidity, which destroys the drug preparations before they reach the bowel. The development and commercialization of both enterically coated drug dosage forms and prodrugs resistant to hydrolysis in the stomach have addressed this.

Enterically coated mesalamine dosage forms include Asacol®, Claversal®, and Pentasa®. Asacol® is coated with a delayed release acrylic resin (Eudrogit-S) that releases the drug in the distal ileum and colon. The resin on Asacol® releases mesalamine in a pH-dependent manner at pH 6 or above, causing release of mesalamine in the distal small bowel and colon making this drug ideal for the treatment of ulcerative colitis. Claversal® is also coated with a delayed release acrylic resin (Eudrogit-L) that releases the drug in the distal ileum and colon. Pentasa® contains ethylcellulose-coated, controlled-release microgranules of mesalamine that release mesalamine in a time-release manner throughout the distal portion of the small and the entire large intestine. Accordingly, Pentasa® would appear suitable for the treatment of Crohn's disease when the distal ileum is affected in addition to its use in ulcerative colitis. Each of these formulations uses a different mechanism to deliver the mesalamine to the sites of inflammation such as distal ileum and colon; however, they were all designed to bypass the areas of rapid absorption and inactivation of mesalamine in the duodenum and the jejunum by releasing the drug lower in the small intestine and colon. Innovative approaches in the development of orally administered mesalamine and its attendant problems are illustrated in U.S. Pat. Nos. 4,980,173, 4,496,553, 4,880,794, and 5,010,069; and the review by Prakash, A and Markham, A in Drugs 57(3): 383–408 (1999).

Attempts to overcome this acidity problem have also included use of the prodrugs sulfasalazine (Azulfidine®), olsalazine (Dipentum®) and balsalazide (Colazide®) that resist stomach acidity to yield free 5-ASA after cleavage by bacterial enzymes in the colon. In addition to the reported adverse side effects, accurate targeting of diseased sites with sulfasalazine, olsalazine and balsalazide is limited by the variations in colonic bacterial flora required for bacterial cleavage of these compounds.

The toxic effects of sulfapyridine are the limiting factor in using sulfasalazine. Common adverse reactions include headache, nausea, anorexia, and dyspepsia. These symptoms relate to plasma levels of sulfapyridine and usually occur at dosages greater than 3 g/day. Because of sulfasalazine's substantial toxicity and the limitation of dosing due to side effects, efforts were made to develop mesalamine products with other delivery systems to prevent proximal small bowel absorption.

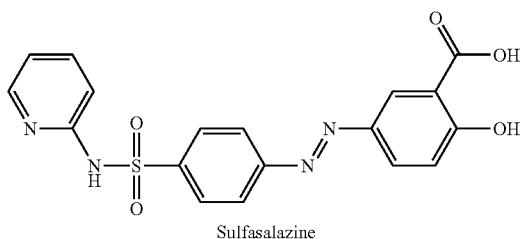

Sulfasalazine

Initially developed in the 1940s for the treatment of rheumatoid arthritis, salicyl-azo-sulfapyridine, or sulfasalazine was quickly recognized as being efficacious in the treatment of colitis. Consisting of a molecule of 5-aminosalicylic acid (5-ASA) joined by an azo bond to a molecule of sulfapyridine, sulfasalazine had, until recently, been a mainstay in the treatment of ulcerative colitis for more than 50 years. The active moiety in sulfasalazine is 5-ASA, with the sulfapyridine acting as a carrier to prevent absorption of 5-ASA in the small bowel. In the distal ileum and colon, bacteria that possess azoreductase, an enzyme in almost all colonic bacteria, split the molecule, releasing free 5-ASA and sulfapyridine. The sulfapyridine is readily absorbed from the colon, acetylated in the liver, and conjugated with glucuronic acid, and excreted in the urine. The 5-ASA is only minimally absorbed, with the majority being excreted in the feces unchanged. 5-ASA's mechanism of action is by direct contact with colonic mucosa to suppress various pro-inflammatory pathways including both cyclooxygenase and lipoxygenase derived products such as prostaglandins and leukotrienes from arachidonic acid and from suppression of superoxide dismutase.

The two newer versions of the azo-linked prodrugs similar to sulfasalazine are olsalazine and balsalazide whose chemical structures are shown below:

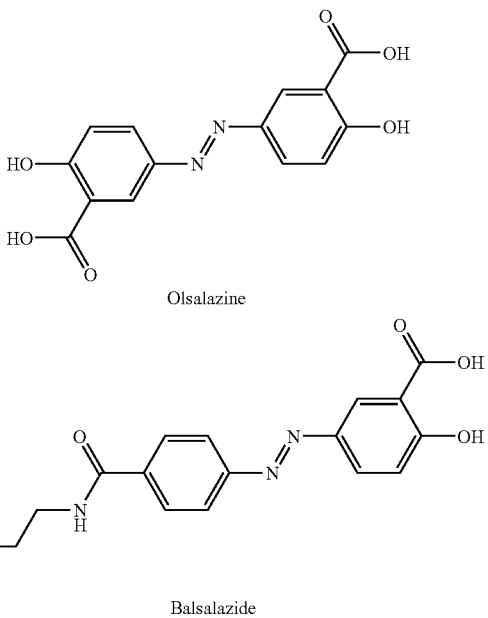

Olsalazine

Balsalazide

The presence of the azo bond in both of these compounds, similar to sulfasalazine's, prevents small-bowel absorption and allows for delivery of the drug mainly in the colon, where bacterial azo reductase liberates the 5-ASA. These drugs would therefore be useful in the same circumstances as sulfasalazine; however, the 5-ASA products may cause diarrhea due to decreased water absorption in the small bowel, most frequently with olsalazine. Since the diseases these drugs are used to treat are diarrheal illnesses, their use may be limited by this untoward effect.

It is well known that the time of transit of matter in the small intestine is limited to about 3–4 hours, whereas the time of transit in the colon is of the order of 20–70 hours. Therefore, controlled-release systems aiming at delivering specific drugs requiring absorption times of more than 3–4 hours have generally relied on colonic delivery. In addition, mesalamine-based drug formulations have generally been designed to target active drug to the colon so that the drug is not destroyed or inactivated by the stomach nor is it rapidly absorbed and metabolized in the upper intestine. Unfortunately, this approach has severely limited the usefulness of mesalamine if the inflammation is in parts of the gastrointestinal tract are not in proximity to the active drug. It is therefore desirable to provide pharmaceutical compositions capable of delivering mesalamine and other topically active pharmacological agents to an inflamed site throughout the gastrointestinal tract whereby the active agent is brought into direct, topical contact with the inflammation.

Crohn's disease is a chronic inflammatory bowel disease that produces patchy, discontinuous inflammation primarily in the small intestine; however, it can produce inflammation in any part of the digestive tract including the mouth esophagus, stomach and colon. This inflammation extends into all layers of the intestinal tissue resulting in pain, diarrhea, gastrointestinal bleeding and malabsorption of nutrients from foods. If the treatment of the inflammation is unsuccessful, the disease progresses and leads to narrowing (stricture) and blocking (obstruction) of the intestinal lumen, the development of abnormal passageways (fistulas) leading from the intestine to another part of the body, and areas of infection (abscesses). It is advantageous to reduce the inflammation associated with the earliest mucosal lesion of Crohn's disease. The earliest mucosal lesion of Crohn's disease is crypt injury in the form of inflammation (cryptitis) and crypt abscesses, which progress to tiny focal aphthoid ulcers, usually located over nodules of lymphoid tissue. As the inflammatory process evolves, the influx and proliferation of macrophages and other inflammatory cells leads to the formation of granulomas. As the disease progresses further, the transmural spread of inflammation leads to bowel wall thickening, deep ulceration, fistulas and abscesses.

It is therefore an object of the present invention to provide site-specific delivery of mesalamine to the inflamed portions of the gastrointestinal tract regardless of location. It is a further object of the present invention to provide site-specific delivery of mesalamine to the inflamed portions of the gastrointestinal tract in those patients with Crohn's disease and ulcerative colitis. It is a further object of the present invention to provide anti-inflammatory agents that are retained at the areas of inflammation for a time effective in reducing the inflammation.

It is a further object of the invention to provide a controlled delivery system which maintains the inflammatory drugs in the small intestine beyond the normal 3–4 hours transit time and allows the required luminal concentration of these drugs to be maintained for more extended periods. It is a further object of the invention to provide a controlled delivery system that maintains the inflammatory drugs in the small intestine and allows the required luminal concentration of these drugs to be maintained for a period from about 4.0 to about 12.0 hours.

A further object of the invention is to ensure accurate and safe delivery of topically active therapeutic agents such as mesalamine to the duodenal, jejunal or proximal small bowel and other segments of the gastrointestinal tract to allow treatment of severe Crohn's ileitis, duodenitis, jejunitis as well as fulminant ulcerative colitis.

In other aspects, the present invention relates to novel compounds useful in the treatment of a variety of ophthalmic disorders, menstruation and menstrual abnormalities, vaginal disorders, intestinal disorders and pelvic inflammatory diseases in which it is desired to provide therapeutic agents that are retained at the diseased areas for a time effective in treating the disorders. It is therefore a further object of the present invention to provide site-specific delivery of therapeutic agents to the diseased areas of the eye, vagina, uterus, upper genital tract and intestine.

BRIEF SUMMARY OF THE INVENTION

In accordance with the present invention, disclosed are compounds having the formula

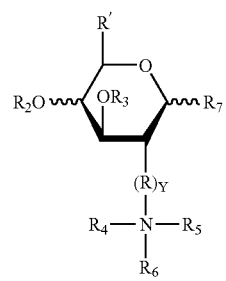

wherein $R_2$ is hydrogen, a monomeric glycoside or an oligomeric glycoside, $R_3$ is hydrogen, a monomeric glycoside, an oligomeric glycoside, or a group having the formula

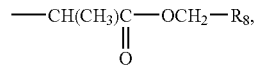

$R$ is a lower alkylene, $R'$ is selected from the group consisting of moieties having the formula

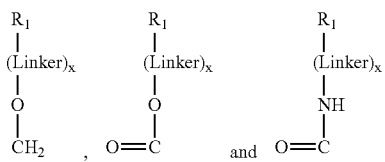

where $X=0$ or $1$, $Y=0$ or $1$, $R_1$ is hydrogen or a pharmacologically active drug residue, $R_8$ a pharmacologically active drug residue, $R_4$, $R_5$, and $R_6$ are independently hydrogen, alkyl, aryl, aralkyl, and cycloalkyl or together form a nitrogen-containing ring selected from the group consisting of

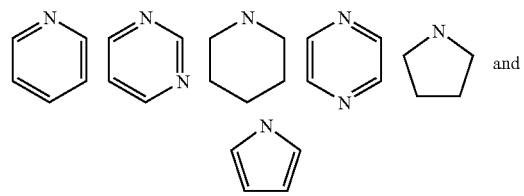

and $R_7$ is hydroxyl or hydroxyalkyl.

DETAILED DESCRIPTION OF THE INVENTION

Figure 1:
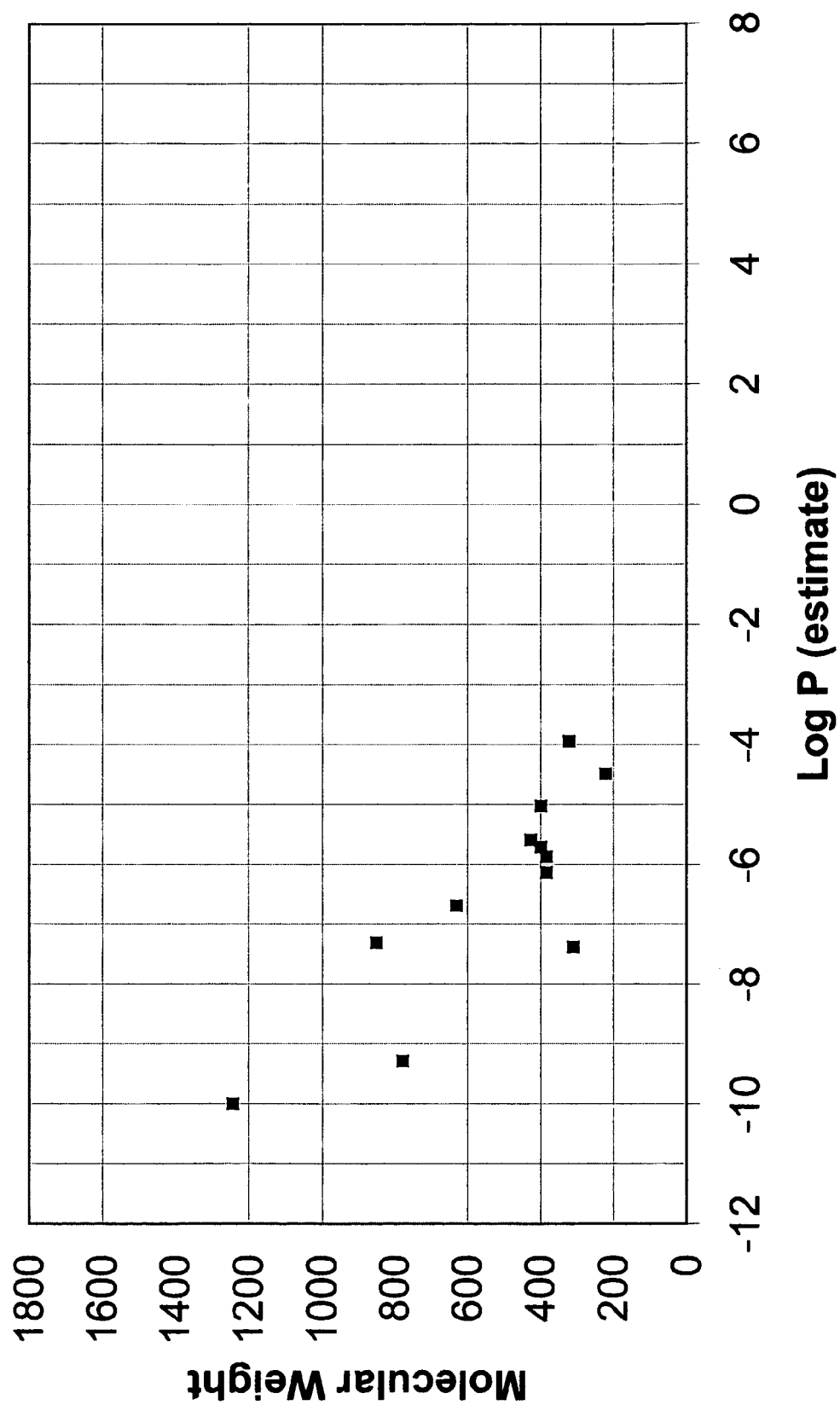
FIG. 1 is a graph showing the relationship between the molecular weight and estimated log P for the bioadhesive saccharides of the present invention.

The present invention relates to novel bioadhesive formulations for the site-adherent, site-retained, sustained drug release of pharmaceutical compounds useful in the treatment of a number of therapeutic disorders including infection, pain, menstrual abnormalities, glaucoma and inflammation. A particular advantage of these bioadhesive formulations is their affinity for the mucosal surface of body cavities that have previously been difficult to access or that have difficulty retaining drugs for therapeutically effective times, either by systemically administered drugs or by topically administered drugs.

In accordance with one aspect, the present invention relates to novel bioadhesive formulations for the site-adherent, site-retained, sustained drug release of anti-inflammatory compounds useful in the treatment of gastrointestinal inflammation. In particular, the invention relates to a controlled drug delivery system for the delivery of anti-inflammatory compounds, particularly mesalamine (5-amino salicylic acid, 5-ASA), 4-amino salicylic acid (4-ASA), and 3-amino salicylic acid (3-ASA) to the entire gastrointestinal (GI) tract in patients suffering from inflammatory diseases of the gastrointestinal tract. The present invention principally relates to the treatment of inflammatory bowel diseases and functional bowel disorders with anti-inflammatory drugs, including but not limited to mesalamine. Unlike conventional and well established treatments, which rely on either timed-release formulations, bacterial enzyme hydrolysis of azo-prodrug compounds or pH dependent release formulations that have restricted access to gastrointestinally inflamed tissue, the compositions of the present invention can target sites throughout the length of the gastrointestinal intestinal tract and consistently deliver the anti-inflammatory agent for a period of time effective in reducing the inflammation.

In accordance with the present invention, the bioadhesive mesalamine formulations have the ability to bind sites within the gastrointestinal tract, are non-toxic and are biocompatible with the human body. In accordance with a preferred embodiment of the present invention, the bioadhesive mesalamine formulations have the ability to bind biological components associated with ulcerations of diseased gastrointestinal membranes. In accordance with a most preferred embodiment of the present invention, the bioadhesive mesalamine formulations have the ability to bind biological components associated with ulcerations of diseased intestinal walls proximal to the distal ileum.

In accordance with another aspect, the present invention includes novel bioadhesive formulations for the site-adherent, site-retained, sustained drug release of therapeutic compounds useful in the treatment of infective, inflammatory and other pathogenic ophthalmic disorders including but not limited to glaucoma, blepharitis, conjunctivitis, dacryocystitis, viral keratitis, bacterial keratitis, fungal keratitis, uveitis, corneal ulcers, endophthalmitis and cellulitis.

In accordance with yet another aspect, the present invention relates to novel bioadhesive formulations for the site-adherent, site-retained, sustained drug release of therapeutic compounds useful in the treatment of pelvic disorders.

In accordance with one aspect of the present invention, the novel bioadhesive formulations are useful in the treatment of pelvic inflammatory disease, an infection of the upper genital tract that can affect the uterus, ovaries and fallopian tubes. In accordance with another aspect of the present invention, the novel bioadhesive formulations are useful in the treatment of pelvic infections.

In accordance with yet another aspect, the present invention relates to novel bioadhesive formulations for the site-adherent, site-retained, sustained drug release of therapeutic compounds administered ocularly for the treatment of systemic disorders.

In accordance with yet another aspect, the present invention relates to novel bioadhesive formulations for the site-adherent, site-retained, sustained drug release of therapeutic compounds useful in the treatment of gastrointestinal oncology disorders such as colon cancer.

In accordance with yet another aspect, the present invention relates to novel bioadhesive formulations for the site-adherent, site-retained, sustained drug release of therapeutic compounds useful in the treatment of menstrual disorders such as dysmennorhhea.

Saccharide Compositions

In accordance with the present invention, a biocompatible, non-toxic drug conjugate is described for the site-specific delivery of pharmacologically effective compounds to a human. Unlike many conventional polymeric drug carriers of the prior art, the drug conjugates of the present invention are characterized by a relatively low molecular weight, the absence of a significant degree of tertiary and quaternary structure normally associated with synthetic polymers or biopolymers, and hydrodynamic properties distinctly different than those of synthetic polymers or biopolymers. The drug conjugates of the present invention are more water-soluble, have lower viscosities and have fewer contaminants than the polymeric drug carriers of the prior art.

The drug conjugates in accordance with the present invention differ from the drug carriers of the prior art in two more aspects. First, the drug conjugates of the present invention are bioadhesive. That is, the drug carriers of the present invention interact with and bind to mucosal layers and biological components associated with inflamed regions of the gastrointestinal tract and ulcerated membranes surrounding the gastrointestinal lumen. Although this bioadhesive property has been demonstrated for a few polymeric materials, it is not generally shared by all. Secondly, the bioadhesive drug conjugates of the present invention are site-specific; however, their adhesion to biological components of the body is electrostatic in nature and is not dependent upon a specific interaction with a specific binding partner, a particular ligand or specific receptor within the body.

There are two major aspects to the development of adhesion between a bioadhesive drug-carrier and the gastrointestinal tissue: (i) the nature of the biological material or tissue with which the bioadhesive drug-carrier comes into contact and ii) the physicochemical characteristics of the bioadhesive material.

In accordance with a preferred embodiment of the present invention, the orally administered bioadhesive mesalamine-conjugates can adhere to the epithelial cell surface of the intestine, the extracellular matrix exposed by delamination of the mucin layer in the diseased portions of the intestine, or to the mucus layer itself. Unlike other site-specific bioadhesives that rely on the presence of specific binding sites, such as membrane-embedded receptors, the bioadhesive mesalamine formulations of the present invention depend an electrostatic interaction with non-specific binding components (such as the mucopolysaccharides, proteoglycans and membrane polysaccharides associated with the cells, the extracellular matrix (ECM), in the intestinal target areas, and the mucin lining adjacent the intestinal target areas).

In accordance with this embodiment of the present invention, the bioadhesive mesalamine formulations perform as site-adherent, site-retained, sustained drug release depots. In the intestine, the dynamics of the lumen and the inflamed intestinal wall can prematurely detach a drug delivery system from its target site. The proliferation, migration and demise of cells in the affected area to which the delivery system adheres can also affect the retention of bioadhesive formulations to the wounded intestinal wall. The fluid dynamics due to the rapid flow of fluids over an area where bioadhesive formulations adhere are expected to vary and affect the retention of these formulations as well. It is important therefore that the electrostatic binding of the mesalamine conjugates be strong. One way to insure high affinity binding is to provide one or more cationic charges to the conjugate in the form of an ionizable amine or quaternized amine. The use of a quaternized amine is preferred in order to insure the electrostatic interaction with the negatively charged components of the target site. Another way to insure high affinity binding is to provide multiple (polyvalent) binding sites. The use of multivalent ligand interaction can increase the overall affinity of the mesalamine conjugates because the equilibrium between association and dissociation of one binding site is greatly influenced by the second binding event at an adjacent site.

In a preferred embodiment of the present invention, the bioadhesive mesalamine conjugates are intended for oral administration. Although orally administered mesalamine formulations are generally designed to by-pass the upper portions of the gastrointestinal tract and increase the absorption of the mesalamine in the intestine or colon, the drug conjugates of the present invention are not limited to colonic or distal ileum targeting and are intended to reduce absorption and metabolism of mesalamine in the more proximal regions of the intestine.

Biological ligands and biopolymers such as epidermal growth factor (EGF), collagen, gelatin, hyaluronic acid, chitin, and high molecular weight chitosan have known ability to bind the membrane-embedded receptors, mucin and the extracellular matrix in the intestine. Although these are of biological origin; they are capable of binding to the mucosal surfaces in intestine; they are biocompatible and biodegradable; they differ considerably from the drug conjugates of the present invention. In particular, these biopolymers are much larger in size, less water-soluble and exhibit different hydrodynamic properties from the drug conjugates of the present invention. For example, hyaluronic acid is a high molecular weight viscoelastic material that adopts a three-dimensional structure in solution that shows extensive intermolecular hydrogen bonding. This, in turn, is believed to restrict the conformational flexibility of the polymer chains and induce distinctive secondary (helical) and tertiary (coiled) interactions. Hyaluronic acid in aqueous solution exhibits a random coil-coil structure with hydrophilic and hydrophobic strands. High molecular weight hyaluronic acid (1,000,000 Daltons) has an intrinsic viscosity of 3,000 ml/g. Hyaluronic acid has been chemically modified to prepare water insoluble gels, films and sponges and has been chemically conjugated to pharmacological agents (Luo, Y and Prestwich, G D, Bioconjugate Chemistry 10:755–763 (1999); Pouyani, T, and Prestwich, G D, Bioconjugate Chemistry 5:339–347 (1994); Kuo, J, Swann, D A and Prestwich, G D, Bioconjugate Chemistry 2:232241 (1991); Luo, Y, Kirker, K P and Prestwich, G D Journal of Controlled Release 69: 169–184 (2000); U.S. Pat. No. 5,356,883; U.S. Pat. No. 5,616,568; U.S. Pat. No. 5,652,347; U.S. Pat. No. 6,013,679; U.S. Pat. No. 6,096,727; U.S. Pat. No. 5,874,417).

Illustrations of high molecular weight polymeric and biopolymer formulations having mucoadhesive potential include those described by Partain et al. (U.S. Pat. No. 4,946,870), Illum (U.S. Pat. Nos. 5,554,388, 5,744,166, 6,391,318, and 6,207,197), Marlin et al. (U.S. Pat. No. 5,645,827), and Mathiowitz (U.S. Pat. No. 6,235,313). Partain et al. disclose film-forming aminopolysaccharides such as high molecular weight chitosium polymers and cationic chitosan derivatives for retaining pharmaceutically active substances at tissue sites. The aminosaccharide chitosan polymers described by Partain et al. have a molecular weight of from 5,000 to over one million Daltons, a solution viscosity (1%, 20°) of from 5 to 5,000 cP and a capacity for a pharmaceutically active compound of up to 5% or so by weight of the chitosan polymer.

Illum discloses polycationic polymers such as high molecular weight diethylaminoethyl dextran (DEAE-dextran), high molecular weight chitosan and other polycationic polymers such as polylysine, polyquaternary compounds., protamine, polyimines, polycationic carbohydrates other than chitosan, polymethacrylate, polyacrylates, polyoxethanes and polyamidoamines for enhancing the absorption of drugs in the intestine. The polycationic polymers described by Illum have a molecular weight of 10,000 to about 500,000, and intrinsic viscosity from about 400 to 1,000 ml/g.

Marlin et al. disclose cationic (quaternary-ammonium) biopolymers such as starch, cellulose, pectin, chitin, guar and chitosan for retaining therapeutically active substances on mucosal surfaces. The polycationic polymers described by Marlin et al. have a molecular weight of 10,000 to about 1,000,000, and viscosities (2%, 250°) from about 5 to 10,000 cP.

In accordance with the present invention, the drug conjugates comprise a pharmacologically active agent covalently attached to saccharides having a molecular weight less than about 2,000 Daltons, including mono-, di-, and oligosaccharides. In accordance with a preferred embodiment of the present invention, the drug conjugates comprise a pharmacologically active agent (drug residue) covalently attached to water-soluble monosaccharides and disaccharides. In accordance with another aspect of the present invention, a pharmacologically active agent is covalently attached to oligosaccharides having from 2 to about 10 glycoside residues. In a preferred embodiment of the present invention, oligosaccharides include those having from 3 to about 8 glycoside residues.

Oligosaccharides useful in the present invention are generally derived by hydrolysis from aminoglycoside-containing polymers including, but not limited to chitin, hyaluronic acid and chitosan. Chitin comprises unbranched chains of β-(1→4)-2-acetamido-2-deoxy-D-glucose. Hyaluronic acid (CAS 9004-61-9) comprises repeating disaccharide units of N-acetyl-D-glucosamine and D-glucuronic acid where the linkage from glucuronic acid to N-acetyl glucosamine is (1→3) and the linkage from N-acetylglucosamine to glucuronic acid is (1→4) resulting in a nomenclature of [→4)-O-(β-D-glucopyranosyl)-(1→3)-O-(2-acetamido-2-deoxy-β-D-glucopyranosyl)-(1→]. Chitosan comprises deacylated unbranched chains of β-(1→4)-2-acetamido-2-deoxy-D-glucose. Illustrative oligoaminosaccharides derived from chitin and mucopolysaccharides useful in the present invention include, but are not limited to, chitosan oligomers, glucosamine (3416-24-8), chondrosine [2-amino-2-deoxy-3-O-β-D-glucopyranosyl-D-galactose], galactosamine (499-14-9), and hyalobiuronic acid [2-amino-2-deoxy-3-O-β-D-glucopyranosyl-D-glucose](13551–21–8). It is generally known in the art that water-soluble oligomeric glycosides can be obtained from chitin after enzymatic hydrolysis using glycosidase, lysozyme or chitinase and deacetylation in acid.

Drug Conjugates

Drug conjugated saccharide compositions in accordance with the present invention include those wherein the anti-inflammatory drug is covalently bound to the hydroxyl group or to the carboxyl group at carbon 6 of the glycoside. The covalent attachment to either the hydroxyl or carboxyl groups can be direct or through a biologically compatible linker molecule. Conjugation to the —CH$_2$OH or —COOH groups of polysaccharides such as hyaluronic acid and others is generally well known, and synthetic procedures for the preparation of these types of drug-conjugated saccharides are described extensively in the patent and scientific literature. Nevertheless, a brief description of the preferred synthetic schemes is illustrated in the following section.

In accordance with one aspect of the present invention quaternized aminoglucosides, including but not limited to the trialkylglucosamines are prepared by alkylation with alkyl halides. For example, trimethylglucosamine saccharides are prepared by methylation with an appropriate amount of methyl iodide.

In accordance with a preferred embodiment of the present invention, direct conjugation of the anti-inflammatory drug mesalamine through the hydroxyl group of a monosaccharide is illustrated below:

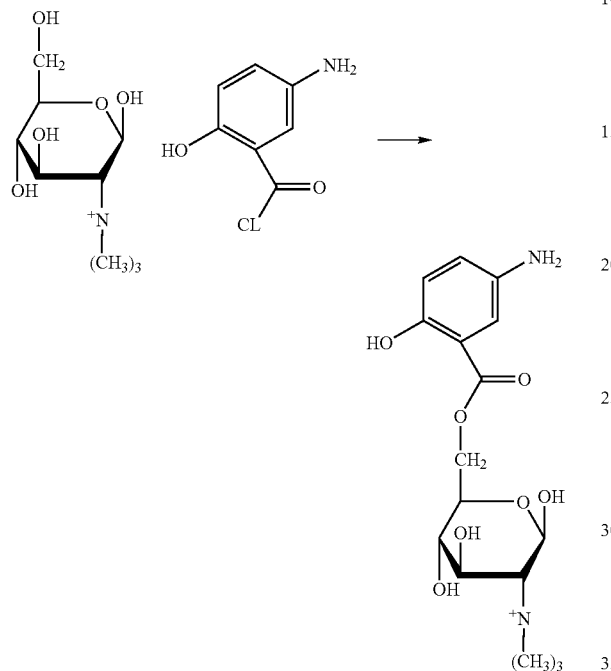

In accordance with another preferred embodiment of the present invention, direct conjugation of the anti-inflammatory drug mesalamine through the carboxyl group of a disaccharide is exemplified below:

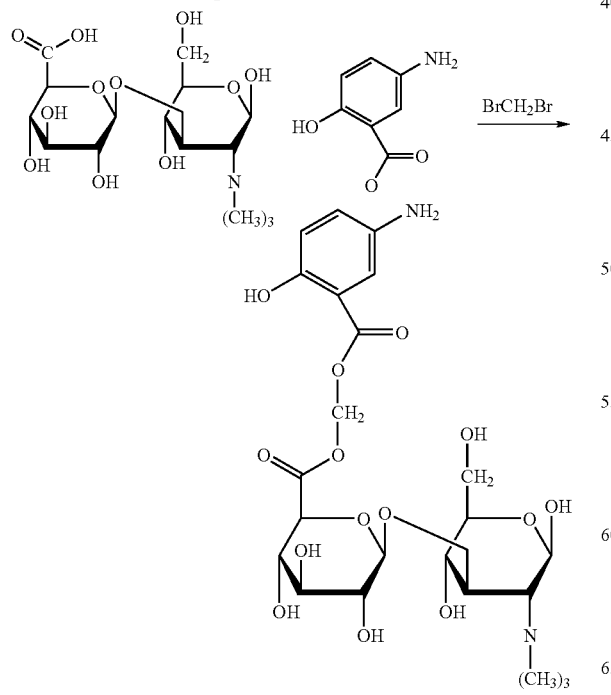

In accordance with another preferred embodiment of the present invention, conjugation of the anti-inflammatory drug mesalamine through a linker to the hydroxyl group of a monosaccharide is exemplified below:

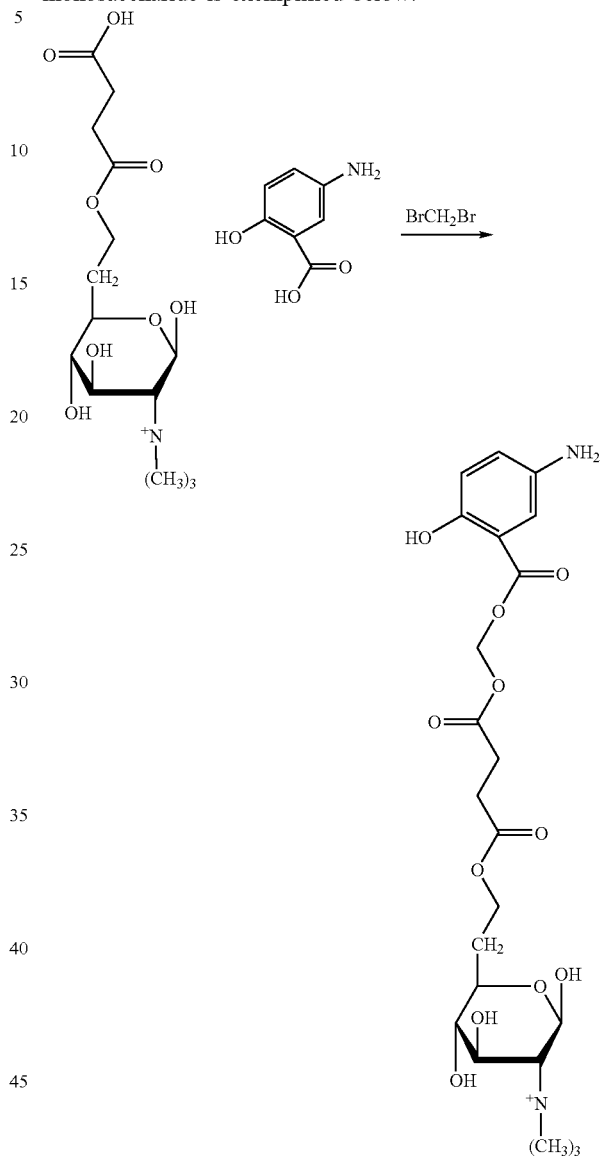

Compounds having the following general formula represent saccharide-based drug-conjugates in one aspect of the present invention:

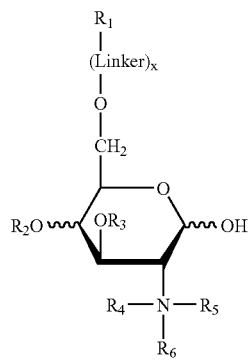

wherein $R_1$ is hydrogen or a pharmacologically active drug residue, $R_2$ is hydrogen or a glycoside having the formula

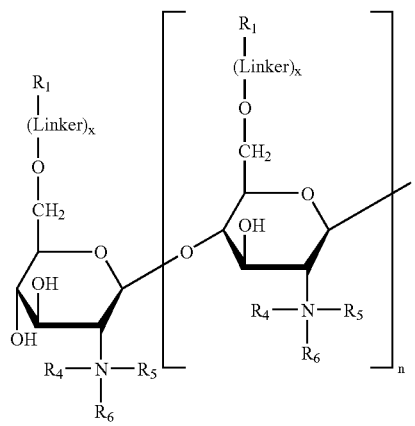

where n=0 to about 8, $R_3$ is hydrogen or a glycoside having the formula

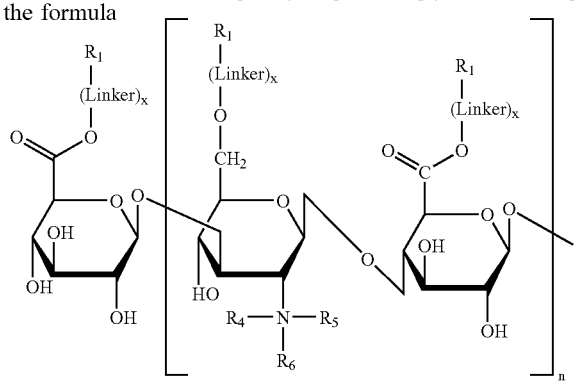

where n=0 to about 8 and where x=0 or 1, and $R_4$, $R_5$, and $R_6$ are independently H, alkyl, aryl, aralkyl, cycloalkyl, or together form a nitrogen containing compound.

In accordance with another aspect of the present invention, a non-specific anchoring group is added to a glycoside pendant group to improve adhesion of the therapeutic compositions to the mucosal surface. This anchoring group can be a saturated or unsaturated alkyl group having a hydrophobic character or a cationic group having a hydrophilic or ionic character. In accordance with one aspect of the present invention, the anchoring group can be an alkyl having from 1 to about 18 carbon atoms or a polyamine linked to the glycoside through an acyl linkage.

A particularly useful glycosidic pendant group for attachment of the anchoring group can be found on carbon six of glucuronic acid. Illustrative disaccharide compounds in accordance with this embodiment of the present invention are shown below:

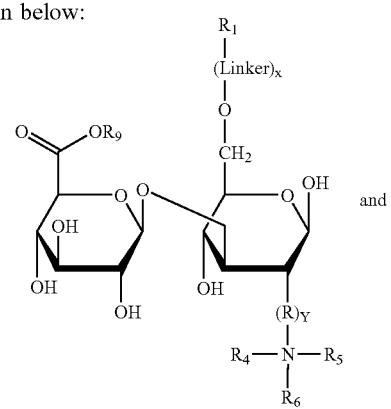

and

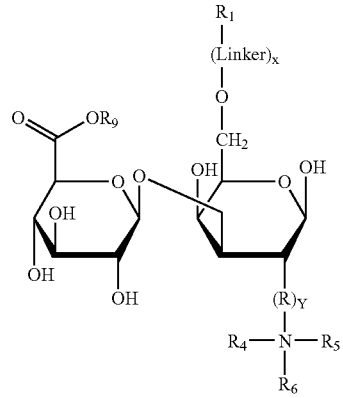

where $R_9$ is an alky, alkylene, monocationic alkylamine or polycationic alkylamine group.

In another aspect of the present invention, oligosaccharide compounds in accordance with this embodiment of the present invention are shown below:

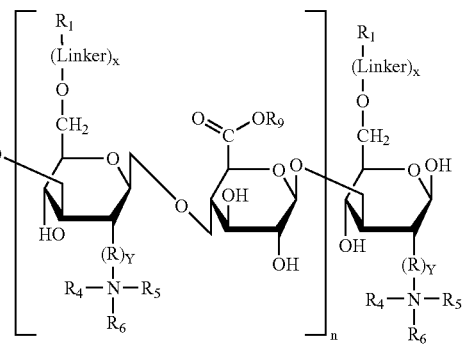

where n is preferably from 1 to about 5.

In accordance with a preferred embodiment of the present invention, $R_9$ is an alkyl, alkylene or polycationic amine group. The alkyl and alkylene groups preferably have from about 1 to about 18 carbon atoms. In one aspect of the present invention, the alkyl or alkylene groups can be long chain moieties and have from 12 to about 18 carbon atoms. In another aspect of the present invention, the alkyl or alkylene groups can be short chain moieties and have from 1 to about six carbon atoms. In a more preferable embodiment of the present invention, $R_9$ is an unsaturated octadecanoic acid residue. The alkyl chain length adds hydrophobicity and the unsaturation provides flexibility of the chain.

In accordance with another aspect of the present invention, $R_9$ is a polycationic alkylamine group. In a preferred embodiment of the present invention, $R_9$ is a polyamine having form 1 to about 18 carbon atoms including but not limited to polysine, polyornithine and aliphatic amines characterized by the repeating group denoted as $—(CH_2CH_2—NH)—$. In accordance with a preferred embodiment, the amine groups of the polyamine are quaternary amines and have a positive charge independent of the pH.

In accordance with another aspect of the present invention, $R_9$ is a positively charged monoamine and includes a choline, or betaine residue.

In accordance with the present invention, R' is selected from the group consisting of

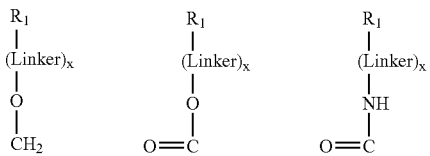

where x=0 or 1. In accordance with the present invention, linker groups include, but are not limited to, carboxylic acid amides, carboxylic acid esters, and carbamates. It will be appreciated that the rate of hydrolysis of each of these groups will differ and result in the in vivo release of the conjugated drug at different times. In accordance with a preferred embodiment of the present invention, R' has the formula

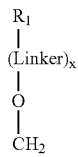

Therapeutic compositions of the present invention are particularly useful for the treatment of disorders at target sites within the body that are difficult to access or that have difficulty retaining topically administered drugs. Examples of non-systemic sites within the body that benefit from the compositions of the present invention include ocular, rectal, vaginal and intrauterine cavities.

In accordance with the present invention, $R_1$ is hydrogen or is a residue of a pharmacologically active compound having anti-inflammatory activity. Representative anti-inflammatory compounds useful in the present invention, include acetylsalicylic acid, indomethacin, sulindac, etodolac, mefenamic acid, tolmetin, ketorolorac, diclofenac, proprionic acid derivatives such as ibuprofen, naproxen, fenoprofen, and ketoprofen.

In accordance with another aspect of the present invention, $R_1$ is hydrogen or is a residue of a pharmacologically active compound having anti-infective activity. Representative antiviral, antibacterial and antifungal compounds useful in the present invention include acyclovir, idoxuridine, ganciclovir, natamycin, metronidazole, quinolones such as ciprofloxacin, ofloxacin, aminoglycosides such as tobramycin (Tobrex®), and cephalosporins.

In accordance with another aspect of the present invention, $R_1$ is hydrogen or is a residue of a pharmacologically active compound having anti-glaucoma activity. Representative anti-glaucoma compounds useful in the present invention, include beta-blockers such as timolol, levobunolol, carteolol and betaxolol.

In accordance with another aspect of the present invention, $R_1$ is hydrogen or is a residue of a pharmacologically active compound effective in treating dysmennorhhea such as levonorgestrel.

In accordance with another aspect of the present invention $R_1$ is hydrogen or is a residue of a pharmacologically active compound having anti-inflammatory activity and is effective in reducing inflammation of the gastrointestinal tract. In accordance with a preferred embodiment of the present invention, $R_1$ is an anti-inflammatory drug residue of a non-steroidal anti-inflammatory drug (NSAID) and includes indomethacin, mesalamine (5-amino salicylic acid, 5-ASA), 4-amino salicylic acid (4-ASA), and 3-amino salicylic acid (3-ASA). As indicated above, mesalamine (5-ASA) is a recognized anti-inflammatory agent that exhibits anti-inflammatory activity in the gastrointestinal tract. The anti-inhibitory activity of mesalamine has been positively correlated with its ability to inhibit prostaglandin and leukotriene synthesis during inflammation. (Prakash, A and Markham, A Drugs 57(3): 383–408 (1999)). Unlike most non-steroidal anti-inflammatory drugs (NDAIDs), mesalamine also inhibits leukotrienes synthesis by inhibiting lipoxygenase, an enzyme that catalyses the formation of leukotrienes and hydroxyeicosatetraenoic acids (HETEs) from arachidonic acid and its metabolites. (American Society of Health System Pharmacists Drug Information pp2669–2673 (2000); Aminosalicylic acids, other than mesalamine, have demonstrated anti-inflammatory activity in addition to antibacterial activity (Delgado, J I and Cerda, J J. Hospital Formulary 26 (June): 466–473 (1991). It has been suggested that the position of the amino group may not be an important determinant of gastrointestinal activity, and that 4-amino salicylic acid (4-ASA) is useful in the reduction of inflammation associated with gastrointestinal inflammation. Para-aminosalicylate sodium (4-ASA; Teebacin), which differs from mesalamine only in the position of the amino group, (para-versus meta-) has been used for many years as an oral preparation for the treatment of tuberculosis. In addition, 4-ASA enemas have been shown to be as effective as hydrocortisone enemas and as effective as mesalamine enemas for the treatment of distal ulcerative colitis. It has also been suggested that 4-ASA is more stable in solution and might have more anti-inflammatory activity than mesalamine. (Tremaine, W J Hospital Formulary 24 (August): 436–440 (1989) American Society of Health System Pharmacists Drug Information pp2669–2673 (2000)).

Para-aminosalicylate (4-ASA, Paser®), is bacteriostatic against *Mycobacterium tuberculosis*, and inhibits the onset of bacterial resistance to streptomycin and ioniazid. Mycobacteria, including mycobacterium paratuberculosis, are believed to be involved in the development of Crohn's disease (Tremaine, W J Hospital Formulary 24 (August): 436–440 (1989)). Para-aminosalicylate's mechanism of action has been postulated to be inhibition of folic acid synthesis and/or inhibition of mycobactin a cell wall component, thus reducing the uptake of tuberculosis (Physician's Drug Reference pp 1569–1570 55$^{th}$ Edition, publ. Medical Economics (2001)).

In accordance with a more preferred embodiment of the present invention, $R_1$ is residue of mesalamine (5-amino salicylic acid, 5-ASA) or 4-amino salicylic acid (4-ASA). In accordance with a most preferred embodiment of the present invention, $R_1$ is a residue of mesalamine (5-amino salicylic acid, 5-ASA). The term drug residue, mesalamine residue, residue of a pharmacologically active compound or like terms refers to that portion of the conjugated compound which upon release from the saccharide conjugate forms a compound that exhibits the known pharmacological activity of the compound.

In accordance with the present invention, $R_4$, $R_5$, and $R_6$ are independently hydrogen (H), alkyl having from 1 to about 6 carbon atoms including but not limited to methyl, ethyl, propyl, butyl, isobutyl, pentyl and hexyl, aryl including but not limited to phenyl and pyridinyl, aralkyl such as benzyl, and cycloalkyl having from about 3 to about 6 carbon atoms including but not limited to cyclopropyl, cyclobutyl, cyclopentyl, and cyclohexyl, or together form a nitrogen containing ring including but not limited to a nitrogen containing ring selected from the group consisting of pyridine, pyrimidine, pyrazine, piperadine, pyrrolidine, and pyrole.

In accordance with a preferred embodiment of the present invention, $R_4$, $R_5$, and $R_6$ are an alkyl having from 1 to about 6 carbon atoms. In a more preferred embodiment of the present invention, $R_4$, $R_5$, and $R_6$ are an alkyl having from 1 to about 3 carbon atoms. In accordance with the most preferred embodiment of the present invention, $R_4$, $R_5$, and $R_6$ are each methyl or ethyl.

In accordance with the present invention, R is an alkylene having from 1 to about 6 carbon atoms. In accordance with the present invention, R can be an alkylene containing only carbon atoms or a heteroalkylene containing carbon, nitrogen and oxygen atoms. Examples of heteroalkylenes are —NHC(O)CH$_2$—. and —NHC(O)CH$_2$CH$_2$—. In a preferred embodiment of the present invention, R is a lower alkylene having from 1 to about 3 carbon atoms. In accordance with a more preferred embodiment of the present invention, R is —CH$_2$ or —CH$_2$CH$_2$—. In accordance with the present invention, Y is 0 or 1. In accordance with a preferred embodiment of the present invention, Y is 0.

In accordance with the present invention, $R_7$ is hydroxyl or is a hydroxyalkyl including but not limited to trihydroxypropyl, tetrahydroxybutyl, pentahydroxypentyl, and hexahydroxyhexyl. In accordance with a preferred embodiment of the present invention, $R_7$ is hydroxyl.

In accordance with the present invention $R_8$ is a residue of a pharmacologically active compound having anti-inflammatory activity and is effective in reducing inflammation of the gastrointestinal tract. In accordance with a preferred embodiment of the present invention, $R_8$ is an anti-inflammatory drug residue of a non-steroidal anti-inflammatory drug (NSAID) and includes indomethacin, mesalamine (5-amino salicylic acid, 5-ASA), 4-amino salicylic acid (4-ASA), and 3-amino salicylic acid (3-ASA). In accordance with a more preferred embodiment of the present invention, $R_8$ is residue of mesalamine (5-amino salicylic acid, 5-ASA), 4-amino salicylic acid (4-ASA), or 3-amino salicylic acid (3-ASA). In accordance with a most preferred embodiment of the present invention, $R_8$ is a residue of mesalamine (5-amino salicylic acid, 5-ASA). The term drug residue, mesalamine residue, residue of a pharmacologically active compound or like terms refers to that portion of the conjugated compound which upon release from the saccharide conjugate forms a compound that exhibits the known pharmacological activity of the compound.

The term "pharmaceutically acceptable salts" includes non-toxic addition salts of the compounds of the invention that are generally prepared by reacting the compound with a suitable organic or inorganic counter ion known in the art. As described in U.S. Pat. No. 4,496,553, oral pharmaceutical compositions useful in the treatment of ulcerative colitis and Crohn's disease comprised mesalamine or a pharmaceutically acceptable salt or ester thereof in admixture with a pharmaceutically acceptable carrier. These salts of mesalamine were addition salts such as hydrochloride; however, it was recognized that any pharmaceutically acceptable non-toxic organic or inorganic acid could be used. Likewise, the compounds of the present invention can be formulated as ordinary oral drugs such as tablets or capsules by admixture with suitable "pharmaceutical carriers" that are well-known in the art, including, but limited to, lactose, maize starch, potato starch and lubricants such as magnesium stearate and talc.

Use of Conjugated Saccharides

In accordance with the present invention, we have developed an oral controlled-delivery system that is particularly suited to provide the delivery of drugs with an extended absorption time in the small intestine. In particular, the present invention provides accurate and safe delivery of locally active therapeutic agents such as mesalamine to the duodenal, jejunal of proximal small bowel and other segments of the lower gastrointestinal tract to allow treatment of severe Crohn's ileitis duodenitis, jejunitis as well as fulminant ulcerative colitis. This is achieved with prodrugs of anti-inflammatory compounds such as mesalamine that are retained in the gastrointestinal lumen by virtue of their molecular properties, including but not limited to hydrophilicity and molecular size.

In accordance with the present invention, a method of treating inflammatory bowel disease or reducing inflammation is described that comprises administering to a patient an inflammation-reducing effective amount of a compound disclosed herein. In accordance with the present invention, the term "treating inflammatory bowel disease" refers to treating patients in need of therapy with compounds of the present invention that results in clinical remission or clinical improvement as measured by a recognized physician's global assessment. For example, the primary outcome measure for treating Crohn's disease is the Crohn's Disease Activity Index (CDAI) that ranges from about 150 for quiescent disease, from about 250 to about 450 for mild-to-moderate disease, to about 600 for severe disease. A reduction in a patient having an elevated CDAI after treatment to a CDAI index value of about 150 generally indicates successful clinical remission or clinical improvement (response).

In accordance with the present invention, the terms "reducing inflammation" or an "inflammation reducing effective amount" refer to treating patients in need of therapy with compounds of the present invention that results in a reduction or attenuation of inflammation. Methods for assessing the reduction or attenuation of inflammation are well known in the art and include endoscopic examination, histological assessment, measurement of laboratory biochemistries such as erythrocyte sedimentation rate (ESR), measurement of C-reactive protein (C-RP), neutrophil disappearance, and magnetic resonance imaging (MRI) that detects the presence of mucosal lesions and blood flow in inflamed tissue.

The compounds of the present invention are characterized by low octanol: water coefficients (log P) and molecular weights greater than about 300 g/mole. The prodrugs of the present invention are further characterized by their functional properties, including but not limited to bioadhesion and controlled hydrolysis of the active anti-inflammatory compounds. Taken together, these unique molecular and functional properties permit the compounds of the present invention to adhere to inflamed sites within the gastrointestinal tract, retain the anti-inflammatory agents within the gastrointestinal lumen so they will not be absorbed and inactivated, and slowly hydrolyze the active compounds over a controlled period of time.

The intestine is divided in the following layers: 1) the mucosa, containing the epithelium (columnar epithelia cells), basement membrane, lamina propria, and muscularis mucosa, 2) the submucosa containing the lymphocytes, macrophages and mast cells, 3) the muscularis propria containing the circular muscular layer, and 4) the serosa containing the longitudinal muscle fibers which forms the outside cover of the intestine.

The intestinal mucosa is formed of a continuous sheet of epithelial cells of absorptive and mucin-secreting cells. Overlying the mucosa is a discontinuous protective coating, the mucus, which is made of more than 95% water, as well as electrolytes, proteins, lipids and glycoproteins. The glycoproteins are responsible for the gel-like characteristics of the mucus. These glycoproteins consist of a protein core with covalently attached carbohydrate chains terminating in either negatively charged sialic acid or fucose groups. The carbohydrate structure of the intestinal mucous glycoprotein is similar to that of the glycoproteins, which are part of the epithelial cell membrane. The negatively charged mucous glycoproteins act as receptors for carbohydrate binding ligands, which have evolved in nature to allow microorganisms and parasites to establish themselves on the gut wall. One function of the mucus is to intercept these ligands and associated ineffective agents and thereby protects the mucosa.

Lining the entire epithelial surface of the small intestine are villi, ranging in length from about 0.5 to 1.5 mm and extending into the lumen. The microvilli average about 1 um in length. The surface epithelial cells of the small intestine are renewed regularly. It takes about every two days for cells in the duodenum to be renewed completely.

The lamina propria is a loose connective tissue composed mainly of fibronectin, proteoglycans, elastin and collagens types I, III, and V. It has a network of capillaries and lymphatics and numerous mesenchymal as well as inflammatory cells, which act in challenging and destroying antigens and other foreign substances such as bacteria. The lamina propria is separated from the submucosa by a thin layer of smooth muscle cells named muscularis mucosa whose characteristic feature is the activity of the smooth muscle cells in the maintenance of the extracellular matrix of the intestinal wall.

The submucosa is a loose connective tissue with many vessels, lymphocytes, macrophages and mast cells. The collagen content differs from that of the skin by a larger amount of type III (20%) and type V (12%) collagens, while 68% is type I collagen.

The intestinal wall comprises a number of unicellular membranes parallel to each other. For a drug molecule to reach the blood, it must penetrate the mucous layer, the brush border, the apical cell surface, the intracellular fluids of these cells, the basal membrane, the basement membrane, the tissue of the lamina propria, the external capillary membrane, the cytoplasm of the capillary membrane and the inner capillary membrane. There are three primary factors governing this absorption process once a drug is in solution; i) the physicochemical characteristics of the drug molecule, ii) the properties of the components of the gastrointestinal fluids, and iii) the nature of the absorbing membrane.

In accordance with the present invention the primary physicochemical properties of a drug molecule influencing its passive absorption into and across the intestinal wall are its octanol: water partition coefficient (log P or $K_{o/w}$) and its molecular weight. Small drug molecules having a molecular weight less than about 300–400 Daltons are separately absorbed through the intestinal membrane through non-continuous small pores (~3–8.5 angstroms radius) in the membrane.

The octanol: water partition coefficient is a physical property used extensively to describe a chemical's lipophilic or hydrophobic properties. It is the ratio of a chemical's concentration in the octanol-phase to its concentration in the aqueous phase of a two-phase stem at equilibrium. Because measured values range at least 12 orders of magnitude, this ratio is commonly expressed as its logarithm (log P). The estimation of log P for the compounds in accordance with the present invention employed the methodology described by Meylan (Meylan, W M, and Howard, P H Journal of Pharmaceutical Sciences 84:83–92). Drug molecules penetrate the lipid-like cell membranes of the gastrointestinal tract in the same relative order as their increasing oil/water partition coefficients. That is, as log P (or $K_{o/w}$) increases, the rate of absorption of the drug increases.

The graph in FIG. 1 shows the relationship between the molecular weight and octanol: water partition coefficient (log P) for the unconjugated saccharide carriers used in the present invention. This graph primarily shows that the majority of the saccharide carriers of the present invention have a molecular weight generally in the range of from about 200 to 1,300 Daltons, and are extremely water-soluble, suggesting that upon release of the anti-inflammatory drug they would not be expected to easily penetrate the lipid-like membranes or transit through the non-continuous small pores of the gastrointestinal tract.

Figure 2:
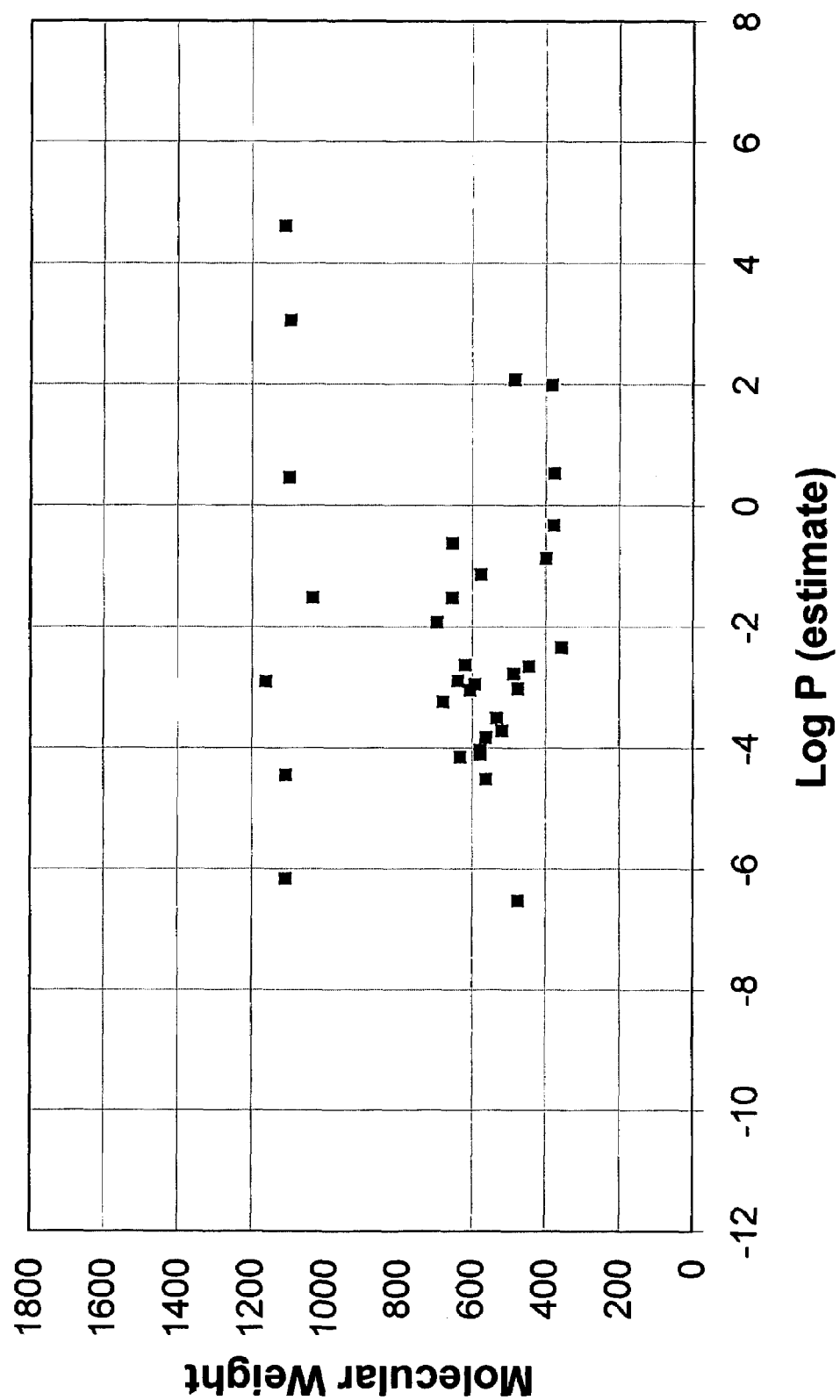
FIG. 2 is a graph showing the relationship between the molecular weight and estimated log P for the bioadhesive saccharide-mesalamine conjugates of the present invention.

The graph in FIG. 2 shows the relationship between the molecular weight and octanol: water partition coefficient (log P) for the conjugated mesalamine-saccharide conjugates of the present invention. This graph primarily shows that the majority of the mesalamine-saccharide conjugates of the present invention have a molecular weight in excess of 350 Daltons and are extremely water-soluble, suggesting that the anti-inflammatory drug-saccharide conjugates would not be expected to easily penetrate the lipid-like membranes or transit through the non-continuous small pores of the gastrointestinal tract. Although not shown in this graph, a number of the drug-saccharide conjugates of the present invention have molecular weights up to about 3,000 Daltons.

Hydrolysis of Mesalamine Conjugates

In accordance with one embodiment of the present invention, the drug conjugates are hydrolyzed into mesalamine and the saccharide conjugate partner in the intestinal lumen. The following illustrative hydrolysis reactions are representative of those expected to occur in the intestine:

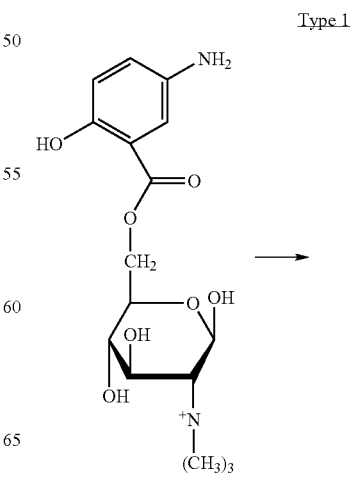

Type 1

-continued
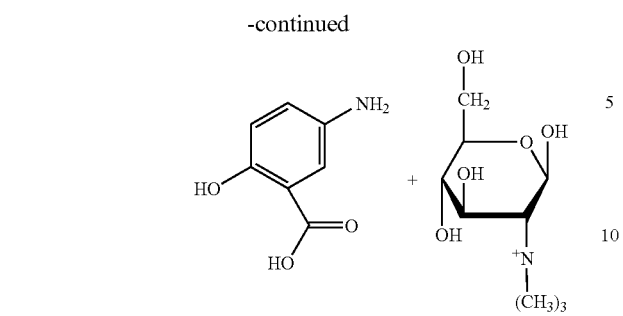
Type 2
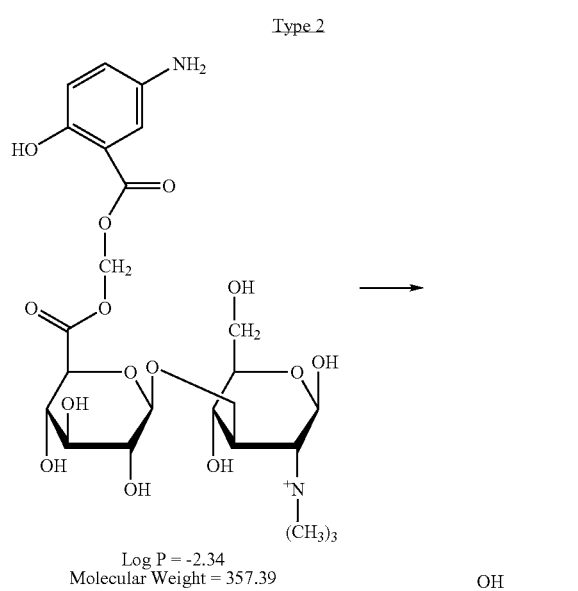
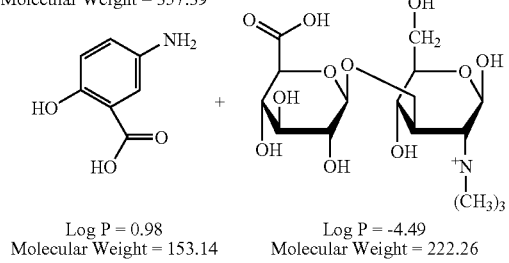
Type 3
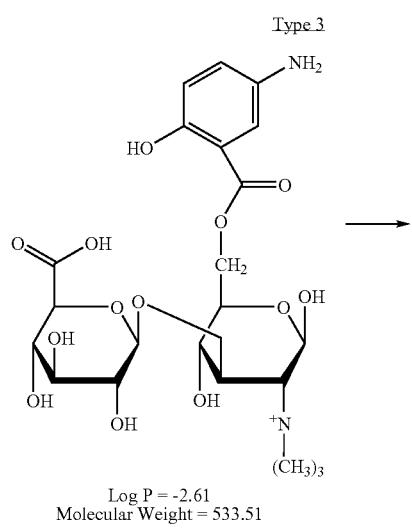
Log P = -2.61
Molecular Weight = 533.51
-continued
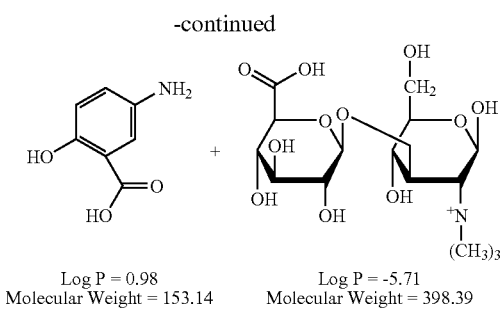
Log P = 0.98
Molecular Weight = 153.14    Log P = -5.71
Molecular Weight = 398.39
Type 4
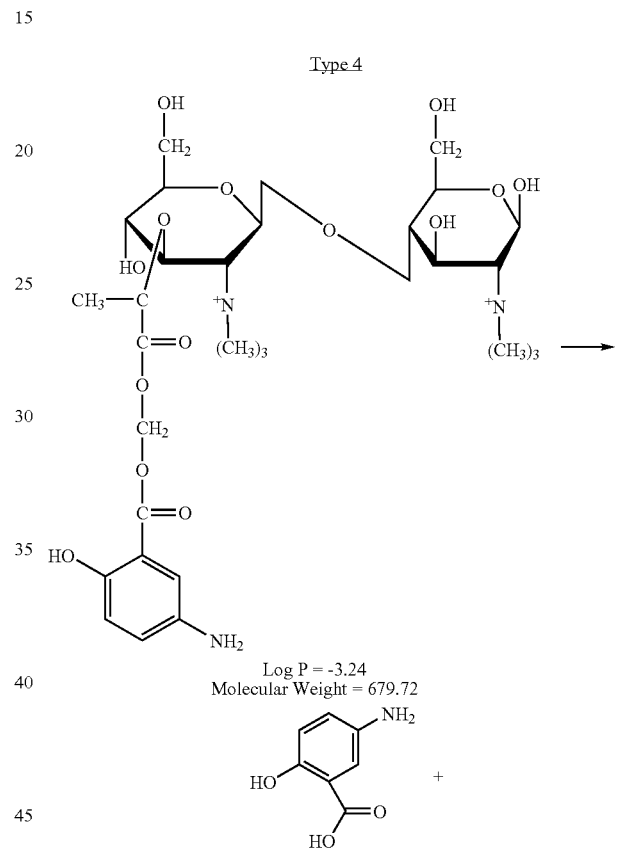
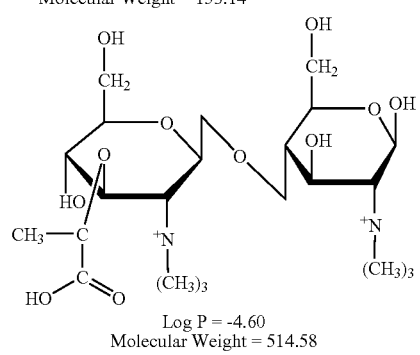
Log P = -4.60
Molecular Weight = 514.58
The release of the anti-inflammatory drugs from the drug-saccharide conjugates of the present invention in the intestinal lumen is expected to be primarily caused by base-hydrolysis. The rate of hydrolysis is expected to be dependent upon several factors including the pH of the lumen and the nature of the covalent attachment of the drug to the saccharide carrier. The pH in several regions of the gastointestinal tract is as follows; about 6.3 in the duodenum, 7.1 in the jejunem, 7.6 in the ielum, and about 8.0 in the ascending colon. The covalent attachment of the drugs to the saccharide carriers in accordance with the present invention is possible through covalent attachment to either the hydroxyl (—CH$_2$OH) or carboxyl groups (—COOH), direct attachment or through a biologically compatible linker molecule, and the attachment to the carboxyl groups (—COOH) through a number of straight or branched chains that affect the hydrolysis rates. For example, the rate of hydrolysis of a drug from a carboxyl ester will be slowed dramatically by increasing the degree of branching and/or by increasing the number of carbon atoms in the linker chain. In this regard, the hydrolysis rates of mesalamine in the present invention are controllable and can be manipulated to release active drug at a rate that will minimize the rapid absorption and inactivation of mesalamine in the duodenum and the jejunum.

The primary distinctions between ulcerative colitis and Crohn's disease exist in the anatomic site affected and the depth of involvement in the mucosal layers. Crohn's disease affects the terminal ileum in up to about 30% of patients, and the colon in about 15% to about 25% of the patients. Overall, about 80% of patients with Crohn's disease have small bowel involvement, and about two-thirds have only small bowel disease. The chronic inflammation in Crohn's disease involves any level of the gastrointestinal tract, and leads to progressive damage in the mucosa, submucosa, the deeper longitudinal muscle layers serosa and regional lymph nodes. Crohn's disease involvement of the mucosa includes confluent linear ulceration patchy, and sharply demarcated granulomas. As the disease progresses, the bowel becomes thickened and leathery, with the lumen becoming increasingly narrower. Lymphoid aggregates increase in the number of smooth muscle cells, and presence of fragmented, disorganized collagen fibers characterizes diseased muscularis mucosa and submucosa. Deep-seated inflammation leads to deep ulcerations leading past the mucosa penetrating into the submucosa and muscularis where fibrosis and fistula form. Neutrophil abscesses affect all layers of the intestine. The course of Crohn's disease is characterized by periods of remission and exacerbation. Although surgery is curative for ulcerative colitis, intestinal resection surgery is not that effective for Crohn's disease and is associated with a high rate of recurrence. The postoperative rate of recurrence is about 85% within three years.

It is believed that mesalamine's mechanism of action is topical (local) rather than systemic. Mucosal production of arachidonic acid metabolites through the cyclooxygenase (prostanoids) as well as the lipoxygenase (leukotrienes and hydroxyeicosatetraenoic acids) is increased in patients with chronic inflammatory bowel disease. It is believed that mesalamine reduces the inflammation by blocking the cyclooxygenase and inhibiting prostaglandin synthesis.

Ulcerative colitis, which is confined to the colon and rectum, causes ulceration of the mucosa and submucosa. The inflammation in ulcerative colitis is more superficial than in Crohn's disease, leads to ulcers that seldom extend beyond the submucosa, and to an increased turnover and depletion of the extracellular matrix. Unlike Crohn's disease, the deeper longitudinal muscle layers serosa and regional lymph nodes are not involved in ulcerative colitis. Ulcerative colitis presents as a relapsing disorder with attacks of bloody mucoid diarrhea followed by asymptomatic periods of varying lengths. The most feared complications of this disease are fulminant colitis and cancer. Ulcerative colitis affects the mucosal layers of the colon and rectum, invariably beginning in the rectum and gradually extending along the colon in a retrograde fashion. Histologically, it is characterized by continuous inflammation with an infiltrate of mononuclear cells, neutrophils, eosinophils and mast cells. Small mucosal hemorrhages may develop suppurative centers, crypt abscesses, which may give rise to small ulcerations, or rupture to underlying tissue.

It is well known that the time of transit of matter in the small intestine is limited to about 3–4 hours, whereas the time of transit in the colon is of the order of 20–70 hours. Therefore, controlled-release systems aiming at delivering specific drugs requiring absorption times of more than 3–4 hours have generally relied on colonic delivery. Another object of the invention is to provide a controlled delivery system which maintains the drug in the small intestine beyond the normal 3–4 hours transit time an allows the required luminal concentration of these drugs to be maintained for more extended periods (e.g. 4.0–12.0 hours).

TABLE 1

| Compound Number | Chemical Name | Molecular Formula | Molecular Composition (Theoretical %) | Molecular Weight |
|---|---|---|---|---|
| 1 | Trimethyl-(2,4,5-trihydoxy-6-hydroxymethyl-tetrahydro-pyran-3-yl)-ammonium | $C_9H_{20}NO_5$ | C(48.64)H(9.07) N(6.30)O(35.99) | 222.26 |
| 2 | [6-Carboxy-4,6-dihydroxy-2-(1,2,3-trihydroxy-propyl)-tetrahydro-pyran-3-yl]-trimethyl-ammonium | $C_{12}H_{24}NO_8$ | C(46.45)H(7.80) N(4.51)O(41.25) | 310.33 |
| 3 | [6-(3-Carboxy-propionyloxymethyl)-2,4,5-trihydroxy-tetrahydro-pyran-3-yl]-trimethyl-ammonium | $C_{13}H_{24}NO_8$ | C(48.44)H(7.50) N(4.35)O(39.71) | 322.34 |
| 4 | [2,4-Dihydroxy-6-hydroxymethyl-5-(3,4,5-trihydroxy-6-hydroxymethyl-tetrahydro-pyran-2-yloxy)-tetrahydro-pyran-3-yl]-trimethyl-ammonium | $C_{15}H_{30}NO_{10}$ | C(46.87)H(7.87) N(3.64)O(41.62) | 384.41 |
| 5 | [2,4-Dihydroxy-6-hydroxymethyl-5-(3-trimethylaminyl-4,5-dihydroxy-6-hydroxymethyl-tetrahydro-pyran-2-yloxy)-tetrahydro-pyran-3-yl]-trimethyl-ammonium | $C_{18}H_{38}N_2O_9$ | C(50.69)H(8.98) N(6.57)O(33.76) | 426.51 |

TABLE 1-continued

| Compound Number | Chemical Name | Molecular Formula | Molecular Composition (Theoretical %) | Molecular Weight |
|---|---|---|---|---|
| 6 | [2,4-Dihydroxy-6-hydroxymethyl-5-(3-trimethylaminyl-4-hydroxy-5-[(3-trimethylaminyl-4,5-dihydroxy-6-hydroxymethyl-tetrahydro-pyran-2-yloxy)-6 hydroxymethyl-tetra-hydro-pyran-2-yoxy]-tetrahydro-pyran-3-yl]-trimethyl-ammonium | $C_{27}H_{56}N_3O_{13}$ | C(51.41)H(8.95) N(6.66)O(32.97) | 630.76 |
| 7 | [2,4-Dihydroxy-6-hydroxymethyl-5-(3-trimethylaminyl-4-hydroxy-5-[-(3-trimethylaminyl-4-hydroxy (3-trimethylaminyl-4,5-dihydroxy-6-hydroxymethyl-tetrahydro-pyran-2-yloxy)-6 hydroxymethyl-tetra-hydro-pyran-2-yoxy]-tetrahydro-pyran-3-yl]-trimethyl-ammonium | $C_{36}H_{74}N_4O_{18}$ | C(50.81)H(8.76) N(6.58)O(33.84) | 851.01 |
| 8 | | $C_{54}H_{110}N_6O_{25}$ | C(52.16)H(8.92) N(6.76)O(32.17) | 1243.50 |
| 9 | [5-(6-Carboxy-3,4,5-trihydroxy-tetrahydro-pyran-2-yloxy)-2,4-dihydroxy-6-hydroxymethyl-tetrahydro-pyran-3-yl]-trimethyl-ammonium | $C_{15}H_{28}NO_{11}$ | C(45.22)H(7.08) N(3.52)O(44.18) | 398.39 |
| 10 | [2,5-Dihydroxy-6-hydroxymethyl-4-(3,4,5-trihydroxy-6-hydroxymethyl-tetrahydro-pyran-2-yloxy)-tetrahydro-pyran-3-yl]-trimethyl-ammonium | $C_{15}H_{30}NO_{10}$ | C(46.87)H(7.87) N(3.64)O(41.62) | 384.41 |
| 11 | [4-(6-Carboxy-3,4,5-trihydroxy-tetrahydro-pyran-2-yloxy)-2,5-dihydroxy-6-hydroxymethyl-tetrahydro-pyran-3-yl]-trimethyl-ammonium | $C_{15}H_{28}NO_{11}$ | C(45.22)H(7.08) N(3.52)O(44.18) | 398.39 |
| 12 | [4-(6-Carboxy-3,4,5-trihydroxy-tetrahydro-pyran-2-yloxy)-2,5-dihydroxy-6-hydroxy methyl-tetrahydro-pyran-3-yl]-trimethyl-ammonium | $C_{15}H_{28}NO_{11}$ | C(45.22)H(7.08) N(3.52)O(44.18) | 398.39 |
| 13 | | $C_{30}H_{54}N_2O_{21}$ | C(46.270)H(6.99) N(3.60)O(43.14) | 778.77 |
| 14 | | $C_{72}H_{146}N_8O_{33}$ | | 1652.00 |
| 15 | [4-(1-Carboxy-ethoxy)-2,5,6-trihydroxy-6-hydroxymethyl-tetrahydro-pyran-3-yl]-trimethyl-ammonium | $C_{12}H_{24}NO_8$ | C(46.45)H(7.80) N(4.51)O(41.25) | 310.33 |

TABLE 2

| Compound Number | Log P[1] | Molecular Weight |
|---|---|---|
| 1 | −4.49 | 222.26 |
| 2 | −4.20 | 310.33 |
| 3 | −3.95 | 322.34 |
| 4 | −6.13 | 384.41 |
| 5 | −5.59 | 426.51 |
| 6 | −6.69 | 630.76 |
| 7 | −7.31 | 851.01 |
| 8 | −10.00 | 1243.50 |
| 9 | −5.02 | 398.39 |
| 10 | −5.87 | 384.41 |
| 11 | −5.71 | 398.39 |
| 12 | −5.71 | 398.39 |
| 13 | −9.29 | 778.77 |
| 14 | | 1652.00 |
| 15 | −7.39 | 310.33 |

[1]Corrected log P - Because the calculation of log P for quaternary-type ammonium compounds ("N + 5") has a very large coefficient, the estimation of log P generally applies only one correction per structure, even if more than quaternary ammonium moiety exists.

TABLE 3

| Compound Number | Chemical Name | Molecular Formula | Molocular Composition (Theoretical %) | Molecular Weight |
|---|---|---|---|---|
| 16 | [6-(5-amino-2-hydroxy-benzoyloxy methyl)-2,4,5-trihydoxy-tetrahydro-pyran-3-yl)-trimethyl ammonium | $C_{16}H_{25}N_2O_7$ | C(53.77)H(7.05) N(7.84)O(31.34) | 357.39 |
| 17 | {6-[3-(5-amino-2-hydroxy-benzoyloxy methylcarbonyl)-propionyloxymethyl]-2,4,5-trihydoxy-tetrahydro-pyran-3-yl}-trimethyl ammonium | $C_{21}H_{31}N_2O_{11}$ | C(51.74)H(6.41) N(5.75)O(36.10) | 487.49 |

TABLE 3-continued

| Compound Number | Chemical Name | Molecular Formula | Molecular Composition (Theoretical %) | Molecular Weight |
|---|---|---|---|---|
| 18 | [6-(5-Amino-2-hydroxy-benzoyloxy methyl)-2,4,5-trihydroxy-tetrahydro-pyran-3-yl]-triethyl-ammonium | $C_{19}H_{31}N_2O_7$ | C(57.13)H(7.82) N(7.01)O(28.04) | 399.47 |
| 19 | [6-(5-Amino-2-hydroxy-benzoyloxymethyl)-2,4,5-trihydroxy-tetrahydro-pyran-3-yl]-tributyl-ammonium | $C_{25}H_{43}N_2O_7$ | C(62.09)H(8.96) N(5.79)O(23.16) | 483.63 |
| 20 | 1-[6-(5-Amino-2-hydroxy-benzoyloxymethyl)-2,4,5-trihydroxy-tetrahydro-pyran-3-yl]-pyridinium | $C_{18}H_{21}N_2O_7$ | C(57.29)H(5.61) N(7.42)O(29.68) | 377.38 |
| 21 | 1-[6-(5-Amino-2-hydroxy-benzoyloxymethyl)-2,4,5-trihydroxy-tetrahydro-pyran-3-yl]-pyrimidin-1-ium | $C_{17}H_{20}N_3O_7$ | C(53.97)H(5.33) N(11.11)O(29.60) | 378.36 |
| 22 | 5-Amino-2-hydroxy-benzoic acid 3,4,6-trihydroxy-5-piperidin-1-yl-tetrahydro-pyran-2-ylmethyl ester | $C_{18}H_{26}N_2O_7$ | C(56.54)H(6.85) N(7.33)O(29.29) | 382.42 |
| 23 | {6-(5-Amino-2-hydroxy-benzoyloxy methyl)-5-[6-(5-amino-2-hydroxy-benzoyloxymethyl)-3,4,5-trihydroxy-tetrahydro-pyran-2-yloxy]-2,4-dihydroxy-tetrahydro-pyran-3-yl}-trimethyl-ammonium | $C_{29}H_{40}N_3O_{14}$ | C(53.21)H(6.16) N( 6.42)O(34.22) | 654.65 |
| 24 | [5-[3-Trimethyamino-6-(5-amino-2-hydroxy-benzoyloxymethyl)-4,5-dihydroxy-tetrahydro-pyran-2-yloxy]-6-(5-amino-2-hydroxy-benzoyloxymethyl)-2,4-dihydroxy-tetrahydro-pyran-3-yl]-trimethyl-ammonium | $C_{32}H_{48}N_4O_{13}$ | C(55.16)H(6.94) N( 8.04)O(29.85) | 696.76 |
| 25 | | $C_{48}H_{71}N_6O_{19}$ | C(55.64)H(6.91) N(8.11)O(29.34) | 1036.13 |
| 26 | | $C_{57}H_{89}N_6O_{19}$ | C(58.90)H(7.72) N(7.23)O(26.15) | 1162.37 |
| 27 | | $C_{54}H_{59}N_6O_{19}$ | C(59.17)H(5.43) N(7.67)O(27.73) | 1096.10 |
| 28 | | $C_{51}H_{56}N_9O_{19}$ | C(55.74)H(5.14) N(11.47)O(27.66) | 1099.06 |
| 29 | | $C_{54}H_{74}N_6O_{19}$ | C(58.37)H(6.71) N(7.56)O(27.36) | 1111.22 |
| 30 | {5-[6-(5-Amino-2-hydroxy-benzoyloxymethoxycarbonyl)-3,4,5-trihydroxy-tetrahydro-pyran-2-yloxy]-2,4-dihydroxy-6-hydroxymethyl-tetrahydro-pyran-3-yl}-trimethyl-ammonium | $C_{23}H_{35}N_2O_{14}$ | C(49.02)H(6.26) N( 4.97)O(39.75) | 563.54 |
| 31 | [6-(5-Amino-2-hydroxy-benzoyloxymethyl)-5-(6-carboxy-3,4,5-trihydroxy-tetrahydro-pyran-2-yloxy)-2,4-dihydroxy-tetrahydro-pyran-3-yl]-trimethyl-ammonium | $C_{22}H_{33}N_2O_{13}$ | C(49.53)H(6.23) N(5.25)O(38.99) | 533.51 |
| 32 | [6-(5-Amino-2-hydroxy-benzoyloxy methyl)-4-(6-carboxy-3,4,5-trihydroxy-tetrahydro-pyran-2-yloxy)-2,5-dihydroxy-tetrahydro-pyran-3-yl]-triethyl-ammonium | $C_{25}H_{39}N_2O_{13}$ | C(52.17)H(6.83) N(4.87)O(36.14) | 575.60 |
| 33 | [6-(5-Amino-2-hydroxy-benzoyloxy methyl)-2,5-dihydroxy-4-(3,4,5-trihydroxy-6-hydroxymethyl-tetrahydro-pyran-2-yloxy)-tetrahydro-pyran-3-yl]-trimethyl-ammonium | $C_{22}H_{35}N_2O_{12}$ | C(50.86)H(6.79) N(5.39)O(36.96) | 519.53 |
| 34 | {6-(5-Amino-2-hydroxy-benzoyloxy methyl)-4-[6-(5-amino-2-hydroxy-enzoyloxymethyl) -3,4,5-trihydroxy-tetrahydro-pyran-2-yloxy]-2,5-dihydroxy-tetrahydro-pyran-3-yl}-trimethyl-ammonium | $C_{29}H_4ON_3O_{14}$ | C(53.21)H(6.16) N(6.42)O(34.22) | 654.65 |
| 35 | {4-[6-(5-Amino-2-hydroxy-benzoyloxymethoxycarbonyl)-3,4,5-trihydroxy-tetrahydro-pyran-2-yloxy]-2,5-dihydroxy-6-hydroxymethyl-tetrahydro-pyran-3-yl}-trimethyl-ammonium | $C_{23}H_{35}N_2O_{14}$ | C(49.02)H(6.26) N(4.97)O(39.75) | 563.54 |
| 36 | {4-[6-(5-Amino-2-hydroxy-benzoyloxymethoxycarbonyl)-3,4,5-trihydroxy-tetrahydro-pyran-2-yloxy]-2,5-dihydroxy-6-hydroxymethyl-tetrahydro-pyran-3-yl}-trimethyl-ammonium | $C_{23}H_{35}N_2O_{14}$ | C(49.02)H(6.26) N(4.97)O(39.75) | 563.54 |

TABLE 3-continued

| Compound Number | Chemical Name | Molecular Formula | Molocular Composition (Theoretical %) | Molecular Weight |
|---|---|---|---|---|
| 37 | (4-{6-[2-(5-Amino-2-hydroxy-benzoyloxy)-ethoxycarbonyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{24}H_{37}N_2O_{14}$ | C(49.91)H(6.46) N(4.85)O(38.78) | 577.57 |
| 38 | (4-{6-[4-(5-Amino-2-hydroxy-benzoyloxy)-butoxycarbonyl]-3,4,5-trihydroxy-tetrahydro-pyran-2-yloxy)2-5-dihydroxy-6-hydroxymethyl-tetrahydro-pyran-3-yl)-trimethyl-ammonium | $C_{26}H_{41}N_2O_{14}$ | C(51.57)H(6.82) N(4.63)O(36.99) | 605.62 |
| 39 | (4-{6-[1-(5-Amino-2-hydroxy-benzoyloxy)-1-methyl-ethoxycarbonyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{25}H_{39}N_2O_{14}$ | C(50.76)H(6.64) N(4.74)O(37.86) | 591.59 |
| 40 | (4-{6-[(5-Amino-2-hydroxy-benzoyloxy)-phenyl-methoxycarbonyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{29}H_{39}N_2O_{14}$ | C(54.46)H(6.15) N(4.38)O(35.02) | 639.64 |
| 41 | | $C_{46}H_{68}N_4O_{27}$ | C(49.82)H(6.18) N(5.05)O(38.95) | 1109.07 |
| 42 | | $C_{46}H_{68}N_4O_{27}$ | C(49.82)H(6.18) N(5.05)O(38.95) | 1109.07 |
| 43 | | $C_{75}H_{125}N_6O_{19}$ | C(63.67)H(8.91) N 5.94)O(21.49) | 1414.86 |
| 44 | | $C_{96}H_{140}N_{12}O_{37}$ | C(56.13)H(6.87) N(8.18)O(28.82) | 2054.24 |
| 45 | (4-{6-[1-(5-Amino-2-hydroxy-benzoyloxy)-ethoxycarbonyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{24}H_{37}N_2O_{14}$ | C(49.91)H(6.46) N(4.85)O(38.78) | 577.57 |
| 46 | | $C_{64}H_{94}N_8O_{26}$ | C(55.24)H(6.81) N(8.05)O(29.89) | 1391.50 |
| 47 | | $C_{128}H_{186}N_{16}O_{49}$ | C(56.25)H(6.86) N(8.20)O(28.69) | 2732.99 |
| 48 | (4-{6-[2-(5-Amino-2-hydroxy-benzoyloxymethyl)-butoxycarbonyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{27}H_{43}N_2O_{14}$ | C(52.34)H(6.99) N(4.52)O(36.15) | 619.65 |
| 49 | (4-{6-[6-(5-Amino-2-hydroxy-benzoylamino)-hexylcarbamoyl]-3,4,5-trihydroxy-tetrahydro-pyran-2-yloxy}-2,5-dihydroxy-6-hydroxymethyl-tetrahydro-pyran-3-yl)-trimethyl-ammonium | $C_{28}H_{47}N_4O_{12}$ | C(53.24)H(7.50) N(8.87)O(30.39) | 631.71 |
| 50 | {4-[1-(5-Amino-2-hydroxy-benzoyloxy methoxycarbonyl)-ethoxy]-2,5,6-trihydroxy-6-hydroxymethyl-tetrahydro-pyran-3-yl}-trimethyl-ammonium | $C_{20}H_{31}N_2O_{11}$ | C(50.52)H(6.57) N(5.89)O(37.01) | 475.48 |
| 51 | [6-(5-Amino-2-hydroxy-benzoyloxy methyl)-4-(1-carboxy-ethoxy)-2,5,6-trihydroxy-tetrahydro-pyran-3-yl]-trimethyl-ammonium | $C_{19}H_{29}N_2O_{10}$ | C(51,23)H(6.56) N(6.29)O(35.92) | 445.45 |
| 52 | (5-{3-Trimethylmino-4-[1-(5-amino-2-hydroxy-benzoyloxymethoxycarbonyl)-ethoxy]-5,6-dihydroxy-6-hydroxymethyl-tetrahydro-pyran-2-yloxy}-2,4-dihydroxy-6-hydroxymethyl-tetrahydro-pyran-3-yl)-trimethyl-ammonium | $C_{29}H_{49}N_3O_{15}$ | C(51.24)H(7.27) N(6.18)O(35.31) | 679.72 |
| 53 | [6-(5-Amino-2-hydroxy-benzoyloxy methoxycarbonyl)-4,6-dihydroxy-2-(1,2,3-trihydroxy-propyl)-tetrahydro-pyran-3-yl]-trimethyl-ammonium | $C_{20}H_{31}N_2O_{11}$ | C(50.52)H(6.57) N(5.89)O(37.01) | 475.48 |

TABLE 4

| Compound Number | Log P[1] | Molecular Weight |
|---|---|---|
| 16 | −2.34 | 357.39 |
| 17 | −2.77 | 487.49 |
| 18 | −0.87 | 399.47 |
| 19 | 2.08 | 483.63 |
| 20 | 0.53 | 377.38 |
| 21 | −0.33 | 378.36 |
| 22 | 1.99 | 382.42 |
| 23 | −1.52 | 654.65 |
| 24 | −1.93 | 696.76 |
| 25 | −1.52 | 1036.13 |
| 26 | −2.90 | 1162.37 |
| 27 | 3.05 | 1096.10 |
| 28 | 0.46 | 1099.06 |
| 29 | 4.61 | 1111.22 |
| 30 | −3.83 | 563.54 |
| 31 | −3.51 | 533.51 |
| 32 | −1.14 | 575.60 |
| 33 | −3.72 | 519.53 |
| 34 | −0.62 | 654.65 |
| 35 | −4.52 | 563.54 |
| 36 | −4.52 | 563.54 |
| 37 | −4.03 | 577.57 |
| 38 | −3.05 | 605.62 |
| 39 | −2.95 | 591.59 |
| 40 | −2.89 | 639.64 |

TABLE 4-continued

| Compound Number | Log P[1] | Molecular Weight |
|---|---|---|
| 41 | −6.16 | 1109.07 |
| 42 | −8.31 | 1109.07 |
| 43 |  | 1414.86 |
| 44 |  | 2054.24 |
| 45 | −4.11 | 577.57 |
| 46 | −2.61 | 533.51 |
| 47 |  | 2737.99 |
| 48 | −2.63 | 619.65 |
| 49 | −4.14 | 631.71 |
| 50 | −3.02 | 475.48 |
| 51 | −2.65 | 445.45 |
| 52 | −3.64 | 679.72 |
| 53 | −6.52 | 475.48 |

[1]Corrected log P - Because the calculation of log P for quaternary-type ammonium compounds ("N + 5") has a very large coefficient, the estimation of log P generally applies only one correction per structure, even if more than quaternary ammonium moiety exists.

Representative compounds of the present invention include, but are not limited to, the following:

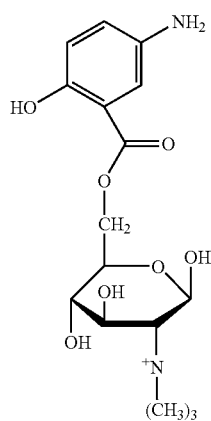

16

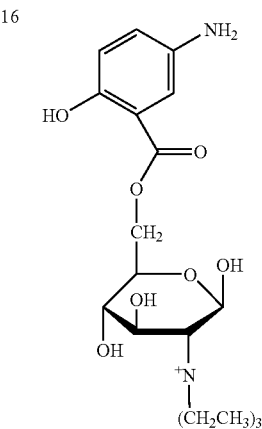

18

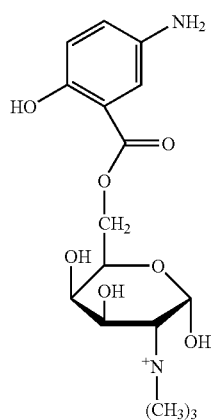

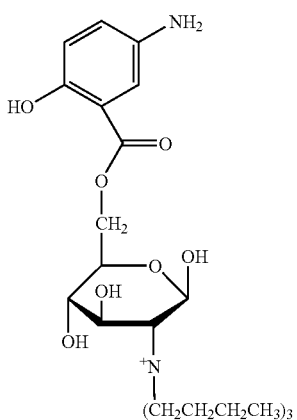

19

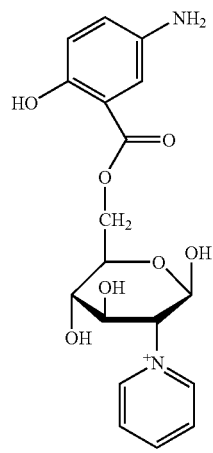 20
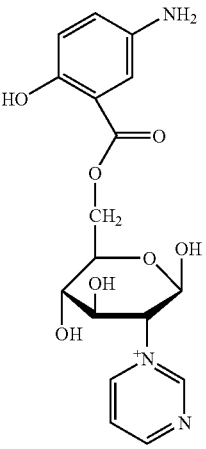 21
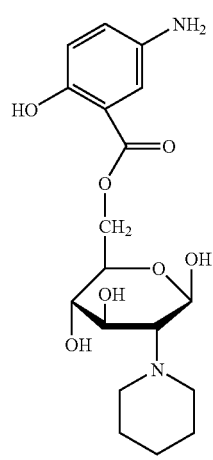 22
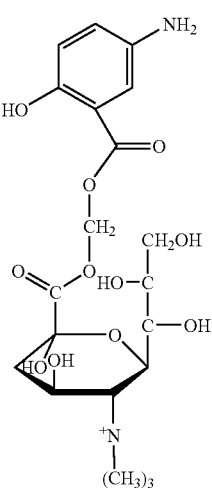 53
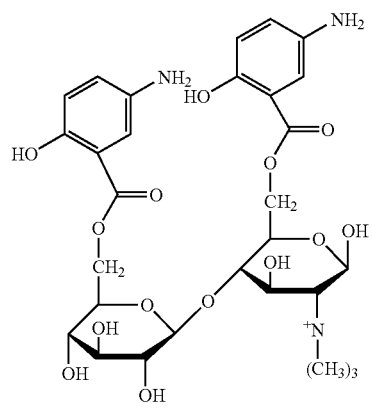 23
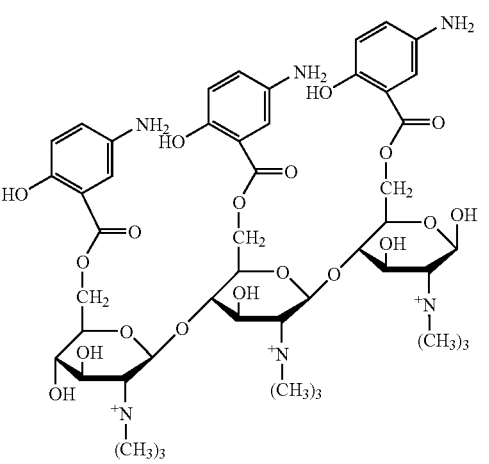 25

-continued
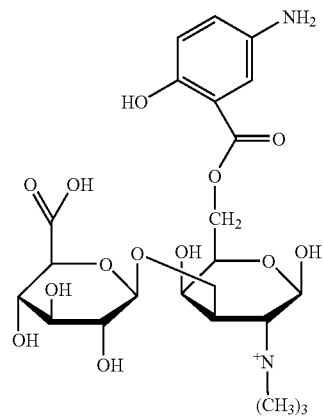
33
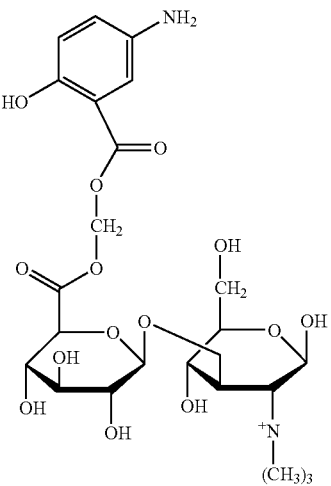
35
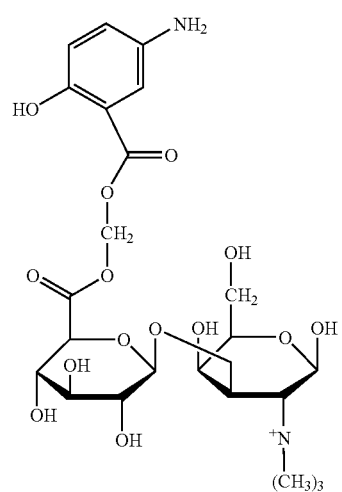
36
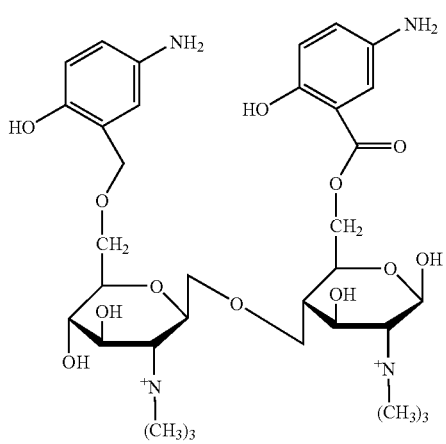
24
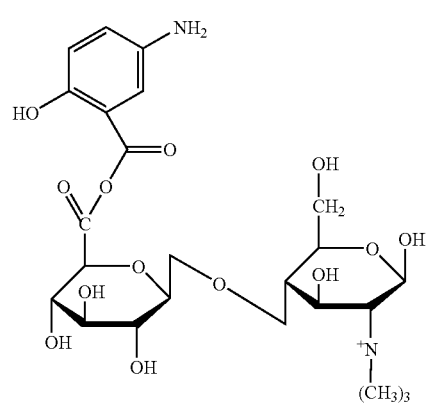
30
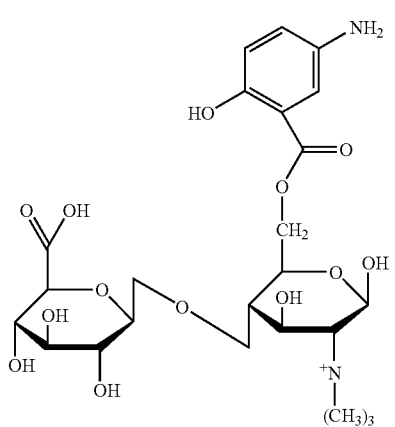
31

-continued
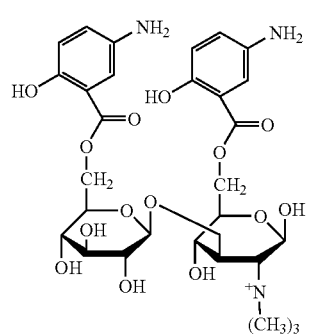
34
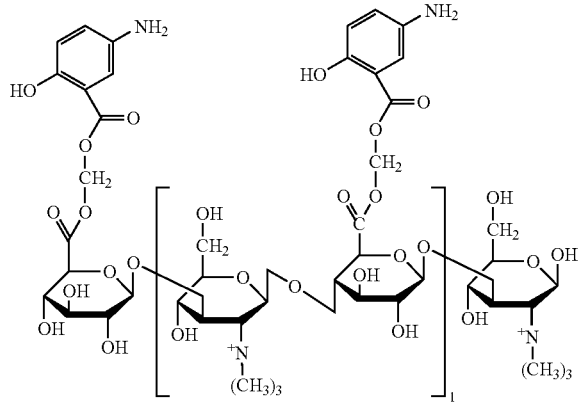
41
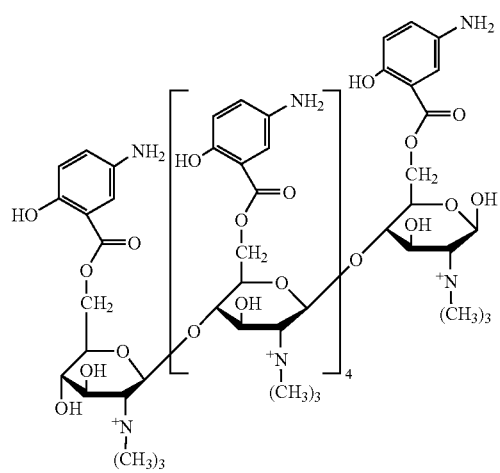
44
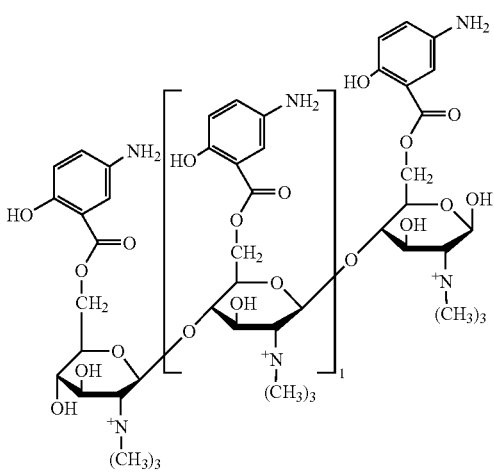
25
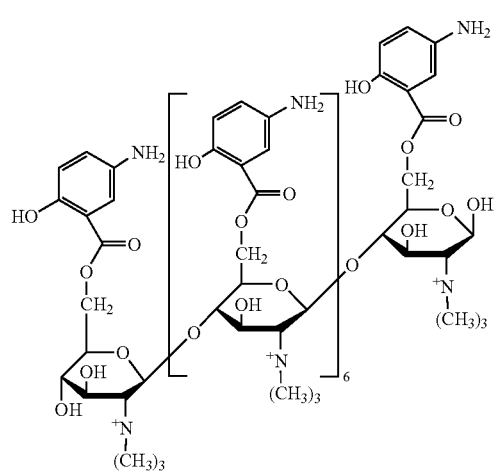
47
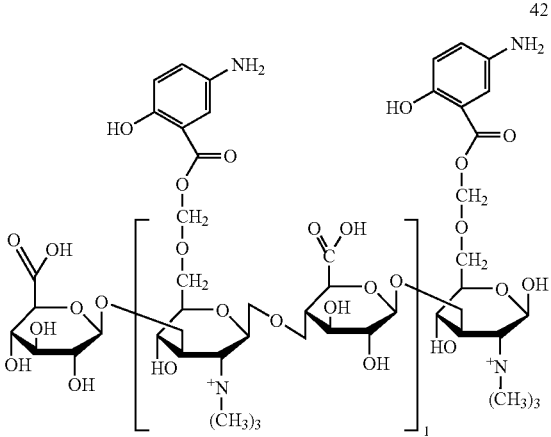
42

-continued
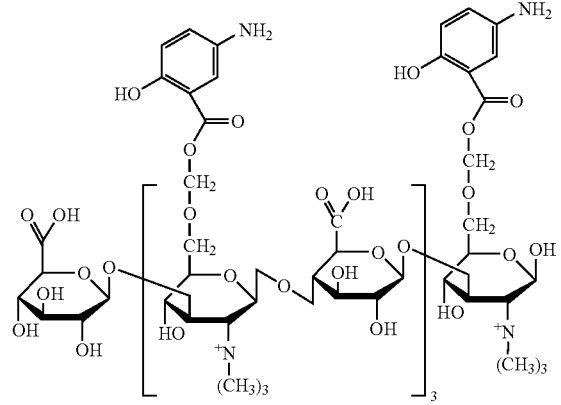
54
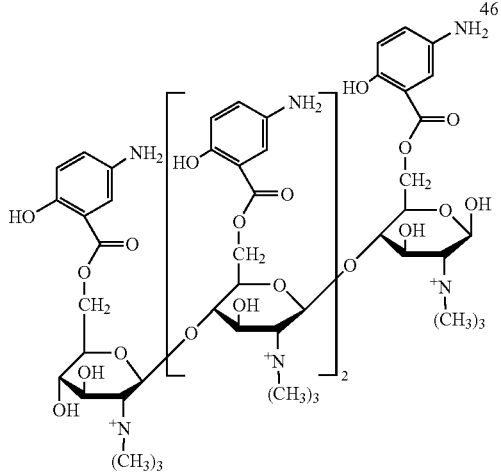
46
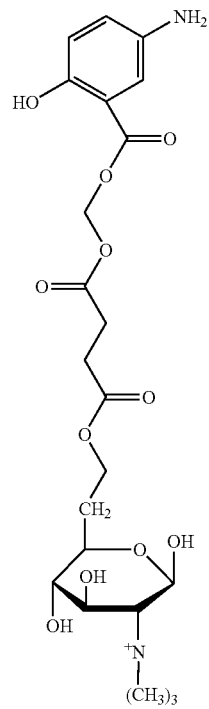
17
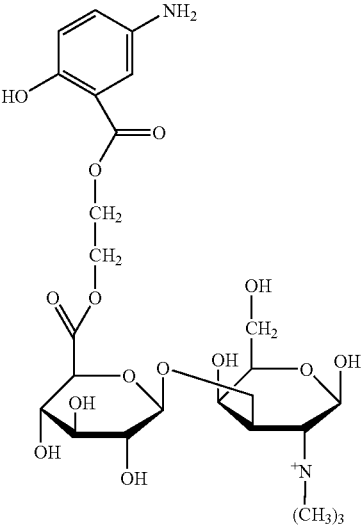
37

-continued
48
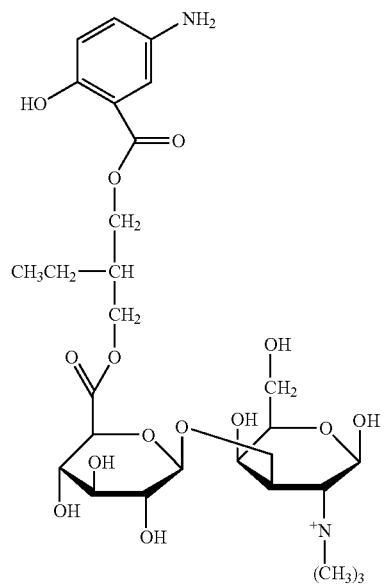
49
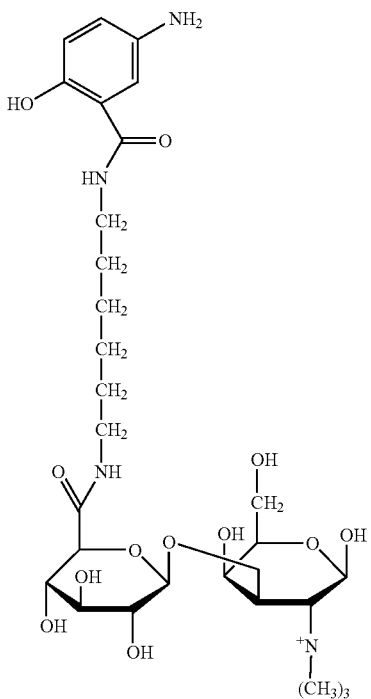
39
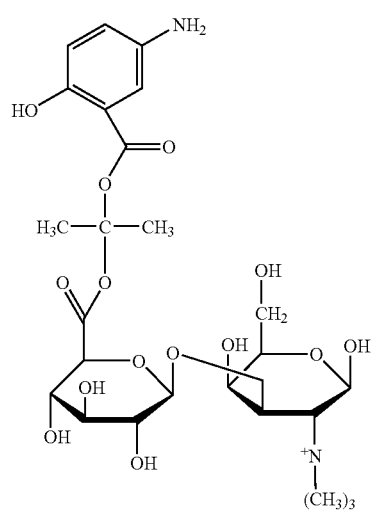
40
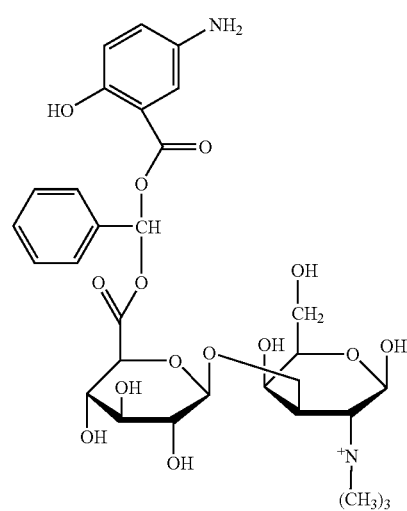

-continued
45
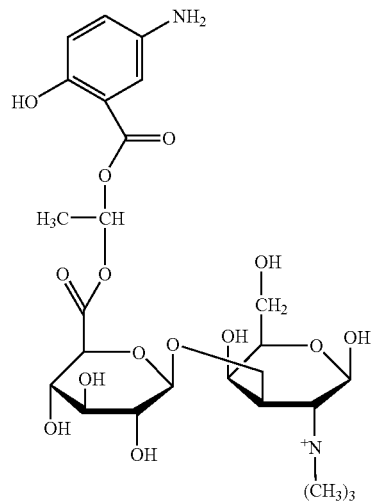
38
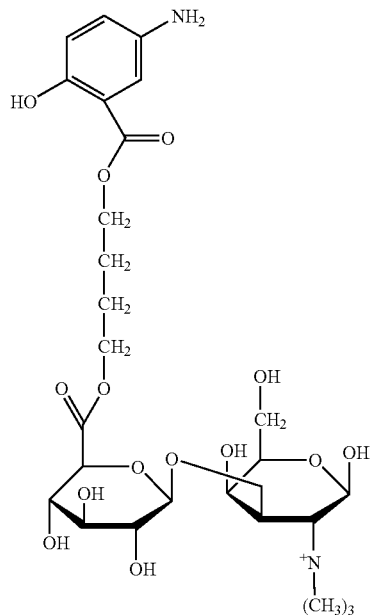
43
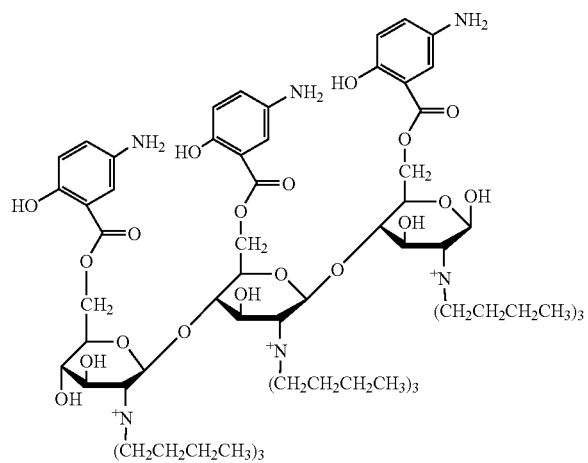
26
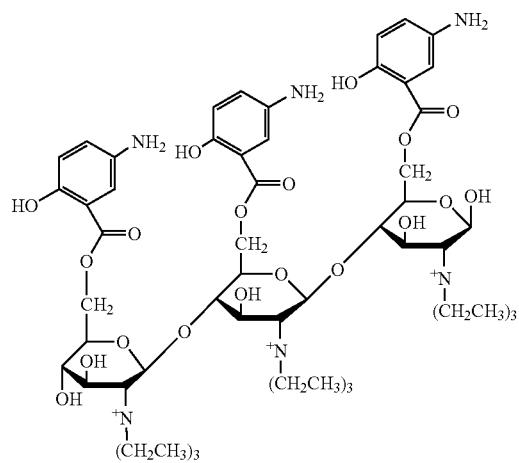
27
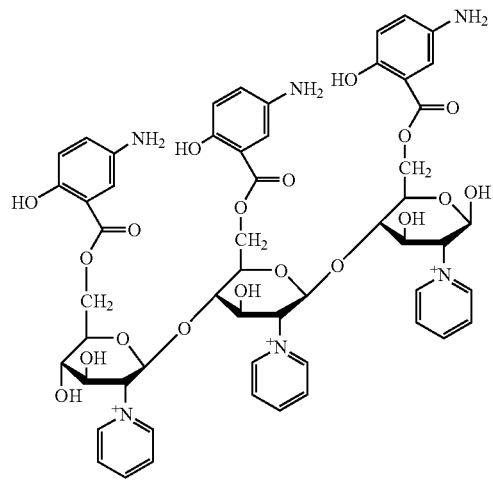
28
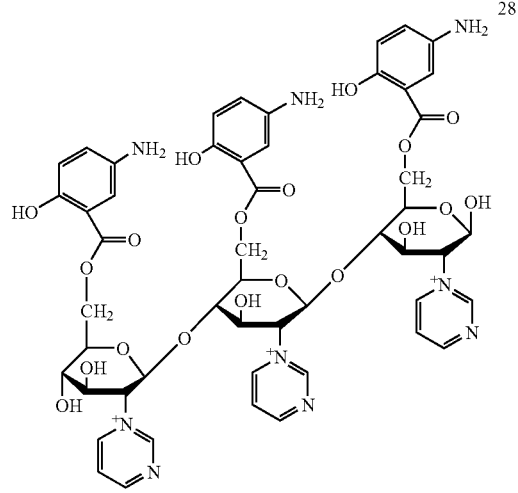

-continued
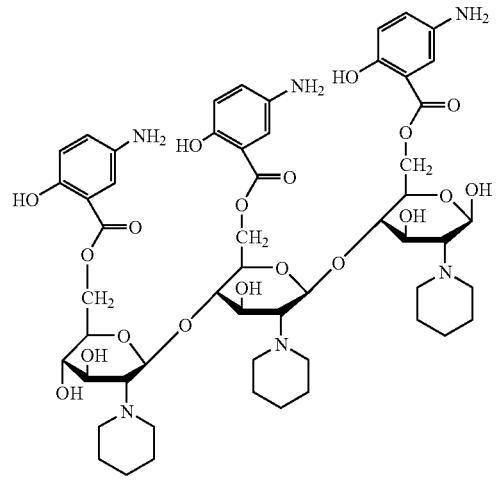
29
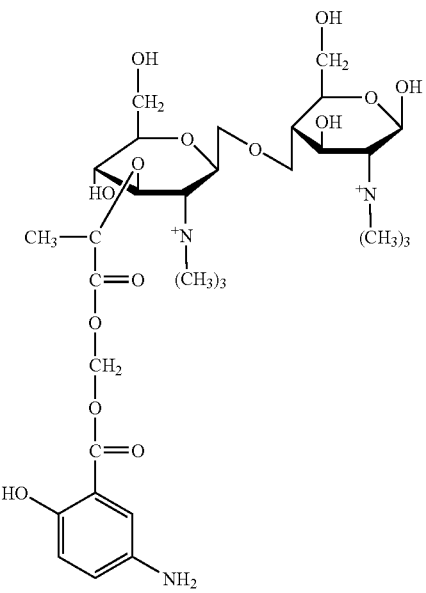
52
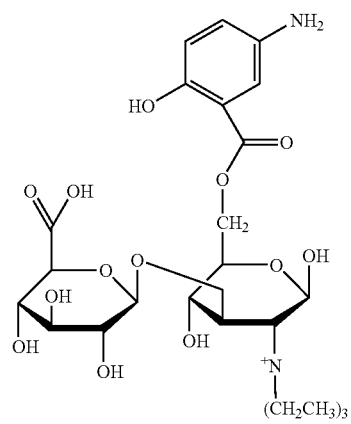
32
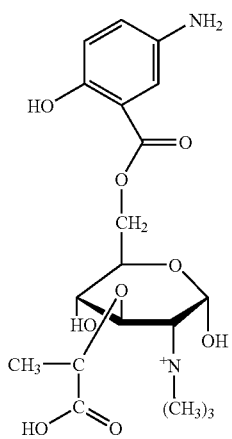
51
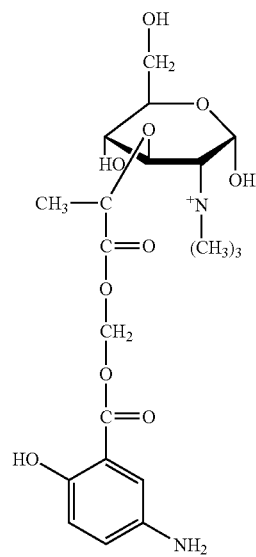
50

The present invention has been described in specific detail and with particular reference to its preferred embodiments; however, it will be obvious to those having skill in the art that modifications and changes can be made thereto without departing from the spirit and scope of the invention.

What is claimed is:

1. A compound having the formula

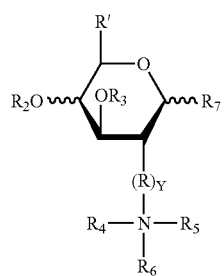

wherein $R_2$ and $R_3$ are independently hydrogen, or a glycoside having the formula

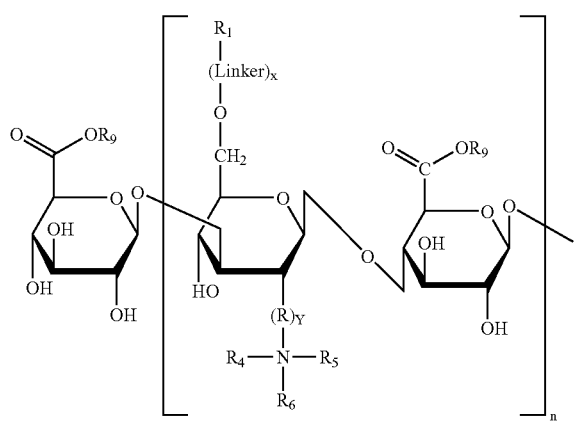

where n=0 to 8 and $R_9$ is an alkyl, alkylene, monocationic alkylamine or polycationic alkylamine, where R is a lower alkylene, where R' is

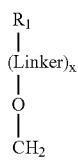

where X=0 or 1, Y=0 or 1, $R_1$ is hydrogen or a pharmacologically active drug residue, and $R_4$, $R_5$, and $R_6$ are independently hydrogen, alkyl, aryl, aralkyl, cycloalkyl or together form a nitrogen-containing ring selected from the group consisting of

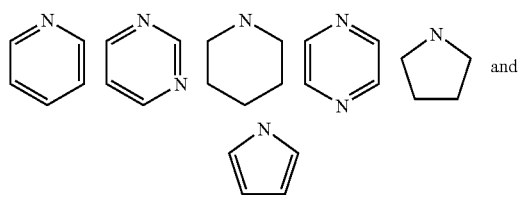

and with the proviso that said compound contains at least one pharmacologically active drug residue, or a pharmaceutically acceptable salt thereof.

2. The compound of claim 1 wherein $R_2$ is hydrogen and $R_3$ is a glycoside having the formula

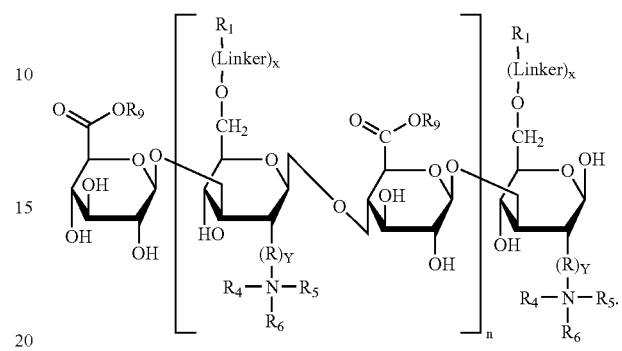

3. The compound of claim 2 wherein $R_3$ is a glycoside having the formula

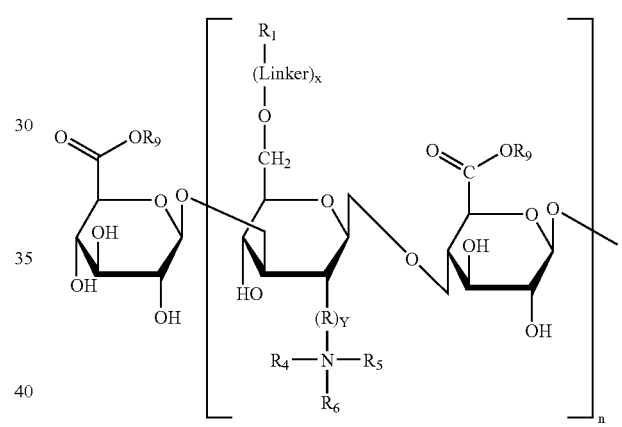

where n=0 to about 8.

4. The compound of claim 2 wherein $R_9$ is a monocationic alkylamine or polycationic alkylamine.

5. The compound of claim 4 wherein the alkylamine is a quaternary amine.

6. The compound of claim 3 having the formula

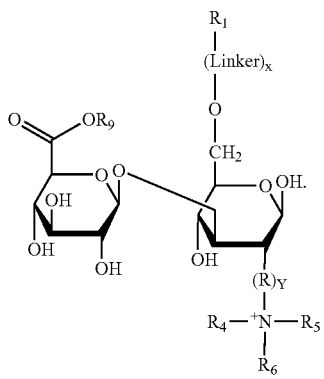

7. The compound of claim 2 having the formula

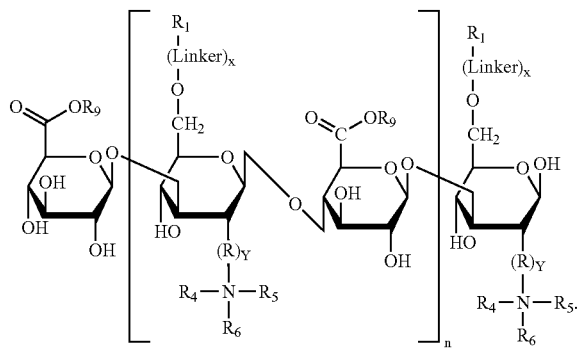

8. The compound of claim 7 wherein $R_9$ is a monocationic alkylamine or polycationic alkylamine.

9. The compound of claim 8 wherein the alkylamine is a quaternary amine.

10. A pharmaceutical composition useful for the treatment of inflammatory disease or for reducing inflammation which composition comprises an inflammation reducing effective amount of a compound having the formula

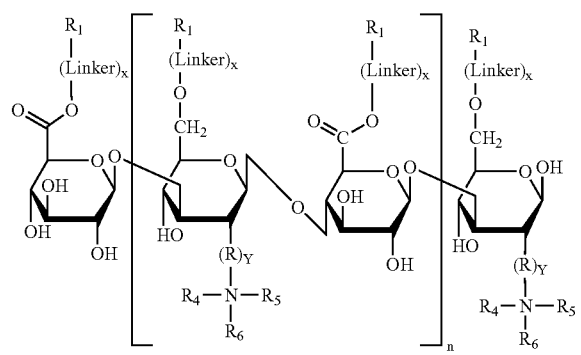

where X=0 or 1, Y=0 or 1, R is an alkylene having from 1 to about 6 carbon atoms or a heteroalkylene containing carbon, nitrogen and oxygen atoms, $R_1$ is hydrogen or a pharmacologically active drug residue, $R_4$, $R_5$, and $R_6$ are independently hydrogen, alkyl, aryl, or aralkyl, and n=0 to about 8, with the proviso that said compound contains at least one pharmacologically active drug residue or a pharmaceutically acceptable salt thereof.

11. The composition of claim 10 comprising a compound having the formula

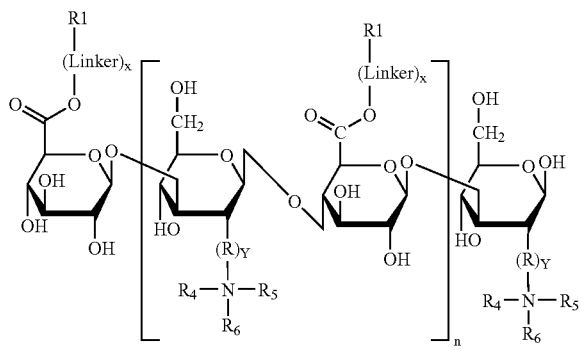

and its pharmaceutically acceptable salt.

12. A pharmaceutical composition useful for the treatment of infectious disease or for reducing infection which composition comprises an infection reducing effective amount of a compound having the formula

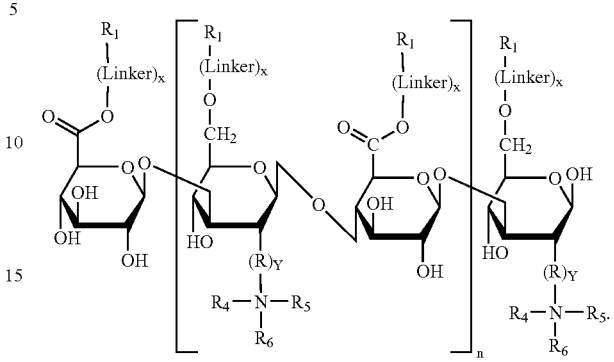

where X=0 or 1, Y=0 or 1, R is an alkylene having from 1 to about 6 carbon atoms or a heteroalkylene containing carbon, nitrogen and oxygen atoms, $R_1$ is hydrogen or a pharmacologically active drug residue, $R_4$, $R_5$, and $R_6$ are independently hydrogen, alkyl, aryl, or aralkyl, and n=0 to about 8, with the proviso that said compound contains at least one pharmacologically active drug residue or a pharmaceutically acceptable salt thereof.

13. The composition of claim 12 comprising a compound having the formula

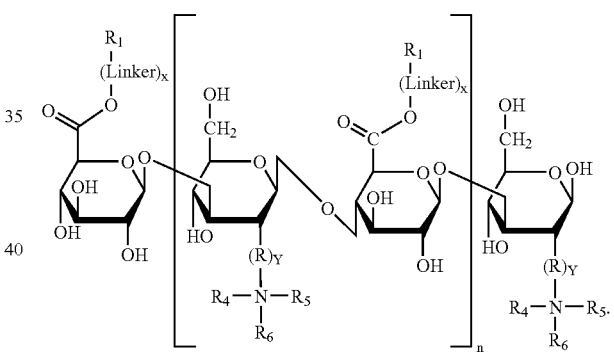

and its pharmaceutically acceptable salt.

14. A pharmaceutical composition useful for the treatment of glaucoma or for reducing intraocular pressure which composition comprises a therapeutically effective amount of a compound having the formula

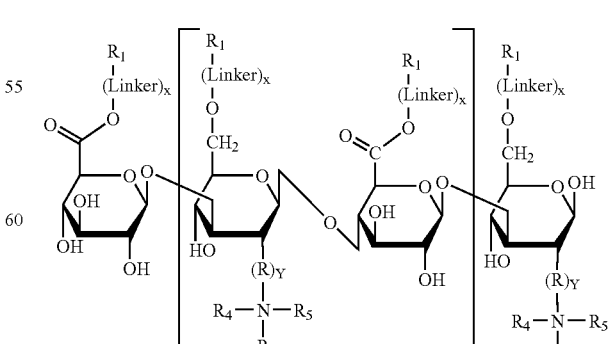

where X=0 or 1, Y=0 or 1, R is an alkylene having from 1 to about 6 carbon atoms or a heteroalkylene containing carbon, nitrogen and oxygen atoms, $R_1$ is hydrogen or a pharmacologically active drug residue, $R_4$, $R_5$, and $R_6$ are independently hydrogen, alkyl, aryl, or aralkyl, and n=0 to about 8, with the proviso that said compound contains at least one pharmacologically active drug residue or a pharmaceutically acceptable salt thereof.

15. The composition of claim 14 comprising a compound having the formula

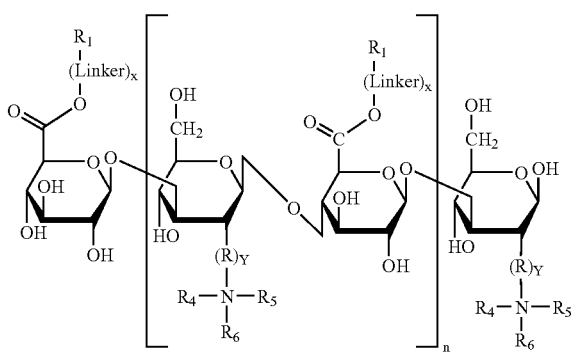

and its pharmaceutically acceptable salt.

16. A pharmaceutical composition useful for administering therapeutic compositions occularly for the treatment of systemic disorders, which composition comprises a therapeutically effective amount of a compound having the formula

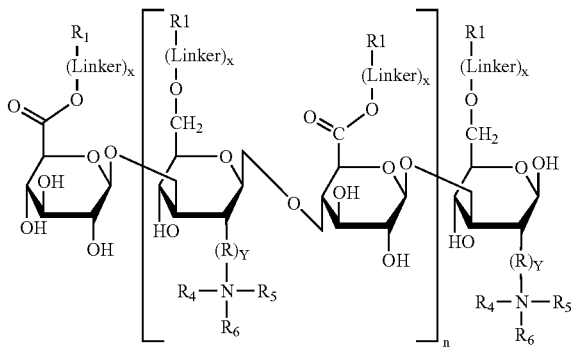

where X=0 or 1, Y=0 or 1, R is an alkylene having from 1 to about 6 carbon atoms or a heteroalkylene containing carbon, nitrogen and oxygen atoms, $R_1$ is hydrogen or a pharmacologically active drug residue, $R_4$, $R_5$, and $R_6$ are independently hydrogen, alkyl, aryl, or aralkyl, and n=0 to about 8, with the proviso that said compound contains at least one pharmacologically active drug residue or a pharmaceutically acceptable salt thereof.

17. The composition of claim 16 comprising a compound having the formula

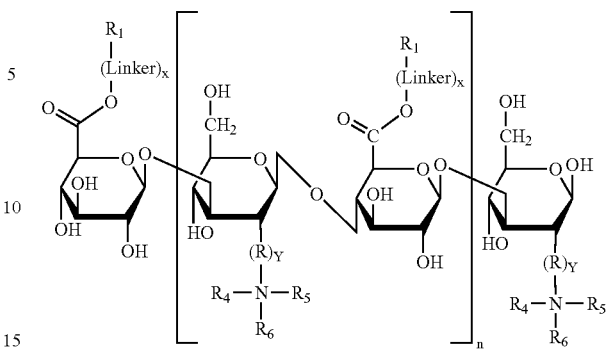

and its pharmaceutically acceptable salt.

18. A pharmaceutical composition useful for the treatment of an oncology disease or for reducing tumors which composition comprises a tumor reducing effective amount of a compound having the formula

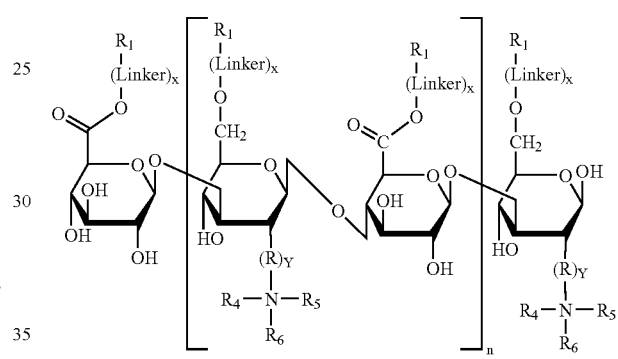

where X=0 or 1, Y=0 or 1, R is an alkylene having from 1 to about 6 carbon atoms or a heteroalkylene containing carbon, nitrogen and oxygen atoms, $R_1$ is hydrogen or a pharmacologically active drug residue, $R_4$, $R_5$, and $R_6$ are independently hydrogen, alkyl, aryl, or aralkyl, and n=0 to about 8, with the proviso that said compound contains at least one pharmacologically active drug residue or a pharmaceutically acceptable salt thereof.

19. The composition of claim 18 comprising a compound having the formula

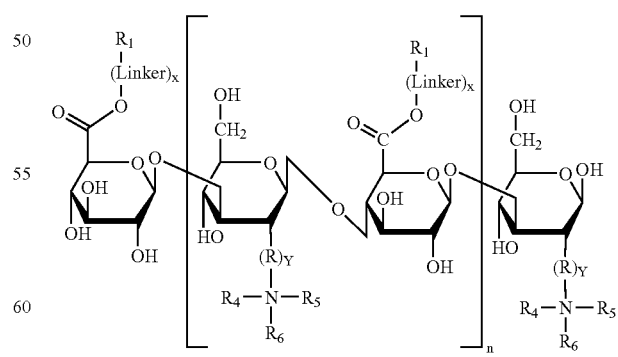

and its pharmaceutically acceptable salt.

* * * * *